(12) United States Patent
Melville et al.

(10) Patent No.: US 7,723,034 B2
(45) Date of Patent: May 25, 2010

(54) METHOD OF SCREENING FOR NEURONAL CEROID LIPFUSCINOSIS IN CANINE BY DETECTING A MUTATION IN CEROID LIPOFUSCINOSIS NEUORNAL 5 (CLN5) GENE

(76) Inventors: Scott Andrew Melville, 83 Malison Street, Wyoming, New South Wales, 2250 (AU); Alan Norman Wilton, Unit 2, 3 Baden Street, Coogee, New South Wales (AU)

(\*) Notice: Subject to any disclaimer, the term of this patent is extended or adjusted under 35 U.S.C. 154(b) by 0 days.

(21) Appl. No.: 11/351,183

(22) Filed: Feb. 9, 2006

(65) Prior Publication Data
US 2006/0218653 A1  Sep. 28, 2006

Related U.S. Application Data

(60) Provisional application No. 60/652,464, filed on Feb. 11, 2005.

(51) Int. Cl.
*C12Q 1/68* (2006.01)
*C07H 21/04* (2006.01)
*C07H 21/00* (2006.01)

(52) U.S. Cl. .................. 435/6; 536/24.3; 536/23.1

(58) Field of Classification Search ........... None
See application file for complete search history.

(56) References Cited

OTHER PUBLICATIONS

Valleno. British J. Haematology. 2004, 128:413-431.*
Fondon et al. PNAS. 2004. 101: 18058-18063.*
Mole et al. Human mutation. 1999. 14:199-215.*
Kopra et al. Hum. Mol. Genetics. 2004. 13: 2893-2906.*

* cited by examiner

*Primary Examiner*—Christine J Saoud
*Assistant Examiner*—Chang-Yu Wang
(74) *Attorney, Agent, or Firm*—Knobbe Martens Olson & Bear LLP

(57) ABSTRACT

The present invention relates to CLN5 nucleic acid and protein variants and functional derivatives, homologues and analogues thereof, together with cellular expression systems, and uses for same. The present invention also provides genetically modified mammalian animals and methods of use thereof. More particularly, the present invention relates to mammalian animals modified to express a mutation in the CLN5 gene, the expression of which variant CLN5 gene induces or otherwise facilitates the onset or progression of a disease condition, and to methods of use thereof. The animals and variant molecules and cells of the present invention are useful in a wide range of applications including, but not limited to, providing a means of diagnosis and means of screening for proteinaceous and non-proteinaceous molecular modulators for use in therapeutic and/or prophylactic applications.

11 Claims, 4 Drawing Sheets

```
>>>>>> PRIMER A >>>>>>
TTTGCTTTGGTGTTCACATAGGTAATTTTTTTTTTTTTAACTAGGAAACACATTTAAC    60
                                                G  N  T  F  N

CAAATGGCAAAGTGGGTAAAGCGGGACAATGAAACAGGAATTTATTACGAGACGTGGACT  120
 Q  M  A  K  W  V  K  R  D  N  E  T  G  I  Y  Y  E  T  W  T

GTTCAAGCCAGCCCAACAAAGGGGGCTGAGACATGGTTTGAATCCTATGATTGTTCTAAA  180
 V  Q  A  S  P  T  K  G  A  E  T  W  F  E  S  Y  D  C  S  K

TTCGTGTTAAGGACATACAAGAAGTTGGCTGAACTTGGAGCAGAGTTCAAGAAGATAGAA  240
 F  V  L  R  T  Y  K  K  L  A  E  L  G  A  E  F  K  K  I  E

<<<<< PRIMER B <<<<<<
ACCAACTATACAAGAATATTTCTTTACAGTGGAGAACCTACCTACTTGGGAAATGAAACC  300
 T  N  Y  T  R  I  F  L  Y  S  G  E  P  T  Y  L  G  N  E  T

TCTATTTTTGGGCCGACAGGAAATAAGACTCTTGCTTTAGCCATAAAAAGATTTTATTAC  360
 S  I  F  G  P  T  G  N  K  T  L  A  L  A  I  K  R  F  Y  Y

CCCTTCAAACCACATTTATCAACTAAAGAATTTCTGCTCAGTATCTTGCAAATTTTTGAT  420
 P  F  K  P  H  L  S  T  K  E  F  L  L  S  I  L  Q  I  F  D

GCAGTGATTATACACAGAGAGTTTTATTTGTTTTATAATTTTGAATATTGGTTTTTACCT  480
 A  V  I  I  H  R  E  F  Y  L  F  Y  N  F  E  Y  W  F  L  P

ATGAAATTTCCTTTTATTAAAATAACATATGAAGAAATCCCTTTACCTAAAAGAAATGAA  540
 M  K  F  P  F  I  K  I  T  Y  E  E  I  P  L  P  K  R  N  E

ACACTTTCTGGTCTATAACATTTTAATTCCATTGCTCTTTTTTCCTTCTGTCACCAGCA  600
 T  L  S  G  L  *

<<< PRIMER C<<
TATATATTTTTCAGGGGGTGATTTTACATTTGTGGATTTCTTAGGCCTTTCTGCCTTGGA  660

<<<<<<
GCAGAA                                                        666
```

FIGURE 2

```
                                                   h
dog       1 ------------------------------------------------MAQAGSADPGV
pig       1 ------------------------------------------------MVPATSTGPGA
human     1 MRRNLRLGPSSGADAQGQGAPRPGLAAPRMLLPPASQASRGSGSTGCSLMAQEVDTAQGA
mouse     1 ------------------------------------------------MLRGCP----C h
dog      12 GGHWAAGPRC--APWRWALALLWLATA------AGGPSRRQWPVPYKRFSFRPEPDPYCQ
pig      12 GVPRCAGVALGRAPWSWETALLWLVAAN--AATAGSRSLRRWPVPYKRFSFRPEPDPYCQ
human    61 EMRRGAGAARGRASWCWALALLWLAVVPGWSRVSGIPSRRSWPVPYKRFDFRPKPDPYCQ
mouse     8 GAHWRP--------ALALALLGLATIDG----ASPTSGQRWPVPYKRFSFRPKTDPYCQ dog      64 AKYTFCPTGSPIPVMKGDDVIEVFRLQTPVWEFKYGNLLGHLKIMHDAIGFRSTLTGKNY
pig      69 AKYTFCPTGSPIPVMKDDDVIEVFRLQAPVWEFKYGDLLGHLKIMHDAIGFRSTLTDKNY
human   121 AKYTFCPTGSPIPVMEGDDDIEVFRLQAPVWEFKYGDLLGHLKIMHDAIGFRSTLTGKNY
mouse    55 AKYTFCPTGSPIPVMKDNDVIEVLRLQAPIWEFKYGDLLGHFKIMHDAVGFRSTLTGKNY h
dog     124 TMEWYELFQLGNCTFPHLRPEMNAPFWCNQGAACFFEGIDDRHWKENGTLVLVATISGNT
pig     129 TMEWYELFQLGNCTFPHLRPEMNAPFWCNQGAACFFEGIDDNHWKENGTLVLVATISGNM
human   181 TMEWYELFQLGNCTFPHLRPEMDAPFWCNQGAACFFEGIDDSHWKENGTLVQVATISGNM
mouse   115 TEEWYELFQLGNCTFPHLRPDKSAPFWCNQGAACFFEGIDDKHWKENGTLSVVATISGNT d              h
dog     184 FNQMAKWVKRDNETGIYYETWTVQASPTKGAETWFESYDCSKFVLRTYKKLAELGAEFKK
pig     189 FNKMAQWVKQDNETGIYYETWTVQASPEKGAETWFESYDCSKFVLRTYEKLAELGAEFKK
human   241 FNQMAKWVKQDNETGIYYETWNVKASPEKGAETWFESYDCSKFVLRTNKLAEFGAEFKN
mouse   175 FNKMAEWVKQDNETGIYYETWTVRAGPGQGASTWFESYDCSNFVLRTYKKLAEFGTEFKK dog     244 IETNYTRIFLYSGEPTYLGNETSIFGPTGNKTLALAIKRFYYPFKPHLSTKEFLLSLLQI
pig     249 TETNYTRIFLYSGEPTYLGNETSIFGPTGNKTLALAIKRFYYPFKPHLSTKEFLLSLLQI
human   301 IETNYTRIFLYSGEPTYLGNETSMFGPTGNKTLGLAIKRFYYPFKPHLPTKEFLLSLLQI
mouse   235 IETNYTRIFLYSGEPIYLGNETSIFGPKGNKTLALAIKRFYGPFRPYLSTKEFLMNFLKI h
dog     304 FDAVIIHREFYLFYNFEYWFLPMKFPFIKITYEEIPLPKRNETLSGL*
pig     309 FDAVIIHRQFYLFYNFEYWFLPMKFPFIKITYEEIPLPQRNKTYFGL*
human   361 FDAVIHHRQFYLFYNFEYWFLPMKFPFIKITYEEIPLPIRNKTLSGL*
mouse   295 FDTVIIHRQFYLFYNFEYWFLPMKPPFIKITYEETPLPTRHTTFFDL*
```

FIGURE 4

METHOD OF SCREENING FOR NEURONAL CEROID LIPFUSCINOSIS IN CANINE BY DETECTING A MUTATION IN CEROID LIPOFUSCINOSIS NEUORNAL 5 (CLN5) GENE

CROSS-REFERENCE TO RELATED APPLICATIONS

This application claims priority under 35 U.S.C. §119(e) to U.S. Provisional Application No. 60/652,464 entitled A NOVEL MOLECULAR VARIANT AND USES THEREOF, filed on Feb. 11, 2005.

FIELD OF THE INVENTION

The present invention relates to CLN5 nucleic acid and protein variants and functional derivatives, homologues and analogues thereof, together with cellular expression systems, and uses for same. The present invention also provides genetically modified mammalian animals and methods of use thereof. More particularly, the present invention relates to mammalian animals modified to express a mutation in the CLN5 gene, the expression of which variant CLN5 gene induces or otherwise facilitates the onset or progression of a disease condition, and to methods of use thereof. The animals and variant molecules and cells of the present invention are useful in a wide range of applications including, but not limited to, providing a means of diagnosis and means of screening for proteinaceous and non-proteinaceous molecular modulators for use in therapeutic and/or prophylactic applications.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge.

Pedigree dog breeds are isolated and inbred populations each of which contain genetic diseases specific to the breed. While these diseases can often be a problem for breeders, they also serve as a valuable resource as models for genetic diseases in humans and other animals. In Australian Border Collies an autosomal recessive mutation resulting in a fatal neurodegenerative disease is wide spread in the population due to the common use of some champion carrier dogs. The condition is a lysosomal storage disorder known as neuronal ceroid lipofuscinosis (NCL), in which subunit c of mitochondrial ATP synthase accumulates (Jolly et al. 1994, *J Small Anim Pract* 35:299-306).

The neuronal ceroid lipofuscinoses are collectively recognized as the most common neurodegenerative disorder in children. Mutations have been identified in six different genes (CLNs 1,2,3,5,6,8) that each result in a unique form of the disease that is distinguishable by the age of onset and clinical course (Mole 1999, *Lancet* 354:443-445). The condition results in the lysosomal accumulation of an autofluorescent lipopigment that is mainly composed of subunit c of mitochondrial ATP synthase (Mole 1999, supra), except for the CLN1 mutation that results in the lipopigment containing high levels of saponins A and D (Tyynela et al. 1993, FEBS Letters 330:8-12). The ultrastructural patterns of these aggregates are variable and dependent on the gene mutated.

The CLN5 protein encodes a soluble lysosomal glycoprotein (Isosomppi et al. 2002, *Hum Mol Genet* 11:885-891) and it is suggested that it interacts directly with the proteins of CLN2 and CLN3 (Vesa et al. 2002, *Mol Biol Cell* 13:2410-2420). The protein displays no significant homology to any of the other NCL genes (Savukoski et al. 1998, *Nature Genet* 19:286-288) and is highly conserved between humans and mice, with the exception of the first exon (Isosomppi et al. 2002, supra; Holmberg et al. 2004, *Neurobiology of Disease* 16:29-40). Four disease causing mutations within the gene have been recorded in humans to date (Savukoski et al. 1998, supra; Holmberg et al. 2000, *Neurology* 55:579-581).

NCL has been identified in a range of animals including cow (Harper et al. 1988, *Acta Neuropathol* 75:632-636), dog (Koppang 1973, Mechanisms of Ageing and Development 2:421-445), horse (Url et al. 2001, *Acta Neuropathol* 101:410-414), and sheep (Jolly 1977, *Med J* 86:304-304; Tyynela et al.), although only in a few cases have the genetic mutations been identified. Naturally occurring NCL mouse models exist for CLN6 (Bronson et al. 1998, *Am J Med Genet* 77:289-297) and CLN8 (Bronson et al. 1993, *Ann Neurol* 33:381-385; Ranta et al. 1999, *Am J Hum Genet* 65:A5-A5), while knockout and targeted disruption models exist for the other identified NCL genes (Mitchison et al. 1999, Neurobiology of Disease 6:321-334; Gupta et al. 2001, *Proc Natl Acad Sci USA* 98:13566-13571; Sleat et al. 2003; Kopra et al. 2004, *Hum Mol Genet* 13:2893-2906). A mutation in CLN6 has been identified as the cause of a late-onset form of NCL in sheep (Broom et al. 1999, *Molecular Genetics and Metabolism* 66:373-375). The first large animal model of CLN5 has been identified recently in Devon cattle in Australia (Houweling et al. 2004).

Animals with NCL have revealed four additional genes as candidates for Border Collie NCL, although no mutations in the human homologues have been identified. Cathepsin D was first detected as a congenital form of the disease in sheep (Tyynela et al. 2000, *Embo J* 19:2786-2792), and further studied using knockout mouse models (Koike et al. 2000, *J Neurosci* 20:6898-6906). Additional mouse models have shown that mutations within PPT2 and CLC-3 also produce NCL (Gupta et al. 2001, supra; Yoshikawa et al. 2002, *Genes Cells* 7:597-605). Additionally, radiation hybrid mapping (Breen et al. 2001, *Genome Res* 11:1784-1795) of the microsatellite markers linked to the English setter NCL gene (Lingaas et al. 1998, *Anim Genet* 29:371-376) indicated the gene is located to a region that does not contain any homologues of any of the identified NCL genes.

Although onset of NCL in Border Collies may be observable to owners as early as 16 months (Studdert and Mitten 1991, *Aust Vet J* 68:137-140), the age of onset and severity can vary greatly between siblings. As the extent of neurodegeneration increases, all affected dogs develop psychological abnormalities and ataxia. The clinical course includes increasing levels of nervousness and possible outbursts of aggression, hallucinations (displayed as fly biting), hyperactivity and epileptic fits. Most animals lose their ability to coordinate everyday muscular activities, such as house training, walking and eating (Studdert and Mitten 1991, supra; Jolly et al. 1994, supra). Complete blindness only occurs in some cases, with changes in the eye only observable through ultrastructural examination of the retina where fingerprint and curvilinear patterns predominated within lysosomal aggregates (Taylor and Farrow 1988, *Acta Neuropathol* 75:627-631). Due to the debilitating nature of the disease, Border Collies suffering from NCL rarely survive beyond 28 months (Studdert and Mitten 1991, supra).

Accordingly, there is an ongoing need to identify the mutations which cause NCL in mammals, and in particular border collies. In work leading up to the present invention, a variant form of CLN5 has been identified, the expression of this variant being associated with the onset of NCL in dogs, in particular in border collies. These findings now provide highly specific genetic and protein based diagnostic means. Since it has been determined that NCL is associated with the expression of this variant form of CLN5, there is also enabled the development and/or use of animal models expressing this CLN5 variant for the development or analysis of, inter alia, therapeutic or prophylactic treatments. Still further, there is also provided means for the in vitro screening for modulatory agents which may be useful for therapeutic or prophylactic application, such as agents which block the expression or functioning of the mutated form of CLN5 thereby enable normalisation of CLN5 levels via administration of the non-mutated protein expression product.

GENERAL

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The subject specification contains nucleotide and amino acid sequence information prepared using the programme PatentIn Version 3.1, presented herein after the bibliography. Each nucleotide and amino acid sequence is identified in the sequence listing by the numeric indicator <210> followed by the sequence identifier (eg. <210>1, <210>2, etc). The length, type of sequence (DNA, protein, etc) and source organism for each nucleotide sequence are indicated by information provided in the numeric indicator fields <211>, <212> and <213>, respectively. Nucleotide and amino acid sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc.). That is, SEQ ID NO:1 as detailed in the specification correlates to the sequence indicated as <400>1 in the sequence listing.

Specific mutations in amino acid sequence are represented herein as "$Xaa_1 n Xaa_2$" where $Xaa_1$ is the original amino acid residue before mutation, n is the residue number and $Xaa_2$ is the mutant amino acid. The abbreviation "Xaa" may be the three letter or single letter amino acid code. A mutation in single letter code is represented, for example, by $X_1 n X_2$ where $X_1$ and $X_2$ are the same as $Xaa_1$ and $Xaa_2$ respectively. In terms of both the mutation and the canine CLN5 nucleotide sequence in general, the nucleic acid residues for canine CLN5 are numbered with the residue cytoseine(c) in the motif tgttcaag (SEQ ID NO. 19) of SEQ ID NO: 1 being referred to in the description as residue number 619. In terms of the CLN5 expression product, the glutamine in the motif Thr Thr Thr Val Gln Ala Ser (SEQ ID NO. 20) of SEQ ID NO:2 is referred to in the description as residue number 207.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| As defined | Xaa | X |

SUMMARY OF THE INVENTION

One aspect of the present invention is directed to a CLN5 protein variant comprising a mutation at amino acid 207 or functionally equivalent residue wherein said variant exhibits altered functional activity relative to wild-type CLN5 or a derivative, homologue or analogue of said CLN5 variant.

Another aspect of the present invention is directed to a canine CLN5 protein variant comprising a mutation at amino acid 207 or functionally equivalent residue wherein said variant exhibits altered functional activity relative to wild-type CLN5 or a derivative, homologue or analogue of said CLN5 variant.

In another aspect there is provided a canine CLN 5 protein variant comprising an amino acid sequence with a deletion of Glutamine 207 or functionally equivalent residue wherein said variant exhibits altered functional activity relative to wild-type CLN5 or a derivative, homologue or analogue of said CLN5 variant.

A further aspect of the present invention provides a canine CLN5 protein variant comprising an amino acid truncation at Glutamine 207, or functionally equivalent residue, wherein said variant exhibits aberrant functional activity relative to wild type CLN5 or a derivative, homologue or analog of said CLN5 variant.

In a another further aspect, the present invention provides:
(i) isolated polypeptides comprising an amino acid sequent substantially as set forth in SEQ ID NO:18 or a polypeptide comprising an amino acid sequence having at least 50%, 60%, 70%, 80%, 90%, 95%, 96%, 97%, 98%, 99% or more sequence identity to SEQ ID NO:18 over a region of 150, 160, 170, 180, 185, 190, 195, 200, 201, 202, 203, 204 or 205 residues or a derivative, homologue or analogue thereof.
(ii) isolated or recombinant polypeptides encoded by a nucleotide sequence as hereinafter described.

In yet another aspect of the present invention is directed to an isolated nucleic acid molecule selected from the list consisting of:

(i) An isolated nucleic acid molecule or derivative, homologue or analogue thereof comprising a nucleotide sequence encoding or complementary to a sequence encoding a CLN5 variant or derivative or homologue of said variant which variant comprises a mutation at amino acid 207 or functionally equivalent residue wherein said variant exhibits altered functional activity relative to wild-type CLN5.

(ii) An isolated nucleic acid molecule or derivative, homologue or analogue thereof comprising a nucleotide sequence encoding or complementary to a sequence encoding a canine CLN5 variant or derivative or homologue of said variant which variant comprises a mutation at amino acid 207 or functionally equivalent residue wherein said variant exhibits altered functional activity relative to wild-type CLN5.

(iii) An isolated nucleic acid molecule or derivative, homologue or analogue thereof comprising a nucleotide sequence encoding or complementary to a sequence encoding a canine CLN5 variant or derivative or homologue of said variant which variant comprises an amino acid sequence with a deletion of glutamine 207 or functionally equivalent residue wherein said variant exhibits altered functional activity relative to wild-type CLN5.

(iv) An isolated nucleic acid molecule or derivative, homologue or analogue thereof comprising a nucleotide sequence encoding or complementary to a sequence encoding a canine CLN5 variant or derivative or homologue of said variant which variant comprises an amino acid sequence with Gln 207 stop wherein said variant exhibits altered functional activity relative to wild-type CLN5.

(v) An isolated nucleic acid molecule or derivative, homologue or analogue thereof comprising a nucleotide sequence encoding or complementary to a sequence encoding a canine CLN5 variant or derivative or homologue of said variant, which variant comprises an amino acid sequence which is truncated at glutamine 207, or functionally equivalent region, of SEQ ID NO: 2 wherein said variant exhibits altered functional activity relative to wild-type CLN5.

(vi) An isolated nucleic acid molecule or derivative, homologue or analogue thereof comprising a nucleotide sequence, or a sequence complementary to said sequence, which sequence comprises a mutation at C619, or functionally equivalent residue, or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of said sequence and/or is capable of hybridising to said sequence under low stringency conditions at 42° C.

(vii) An isolated nucleic acid molecule or derivative, homologue or analogue thereof comprising a nucleotide sequence, or a sequence complementary to said sequence, which sequence comprises a substitution at C619, or functionally equivalent residue, or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of said sequence and/or is capable of hybridising to said sequence under low stringency conditions at 42° C.

(viii) An isolated nucleic acid molecule or derivative, homologue or analogue thereof comprising a nucleotide sequence, or a sequence complementary to said sequence, which sequence comprises a C619 and substitution, or functionally equivalent residue, or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of said sequence and/or is capable of hybridising to said sequence under low stringency conditions at 42° C.

(ix) An isolated nucleic acid molecule or derivative, homologue or analogue thereof comprising a nucleotide sequence encoding, or complementary to a sequence, encoding an amino acid sequence substantially as set forth in SEQ ID NO:18 or a derivative or homologue thereof, or an amino acid sequence having at least 50%, 60%, 70%, 80%, 90%, 95%. 96%, 97%, 98%, 99% or more sequence identity to SEQ ID NO:18 over a region of 150, 160, 170, 180, 185, 190, 195, 200, 201, 202, 203, 204 or 205 residues of SEQ ID NO:17 and/or is capable of hybridizing to said nucleic acid molecule under low stringency conditions at 42° C.

(x) An isolated nucleic acid molecule or derivative, homologue or analogue thereof comprising a nucleotide sequence encoding, or complementary to a sequence, wherein said nucleotide sequence is substantially as set forth in SEQ ID NO:17 or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1030, 1040, 1045, 1050, or 1052 residues of SEQ ID NO:17 and/or is capable of hybridising to SEQ ID NO:17 or complementary form thereof under low stringency conditions at 42° C.

(xi) An isolated nucleic acid molecule or derivative, homologue or analogue thereof comprising a nucleotide sequence as set forth in SEQ ID NO:17.

Still another aspect of the invention is a computer readable medium having recorded thereon at least one nucleic acid and/or polypeptide sequence of the invention.

Still yet another aspect of the present invention is directed to a non-human mammal comprising a CLN5 nucleic acid molecule variant wherein said mammal is characterised by an aberrant CLN5 functional activity phenotype.

Yet still another aspect of the present invention is directed to a non-human mammal comprising a CLN5 nucleic acid molecule variant wherein said mammal is characterised by the onset or predisposition to the onset of, one or more symptoms of NCL or is a carrier of NCL.

In a further aspect there is provided a non-human mammal selected from the list:

(i) a non-human mammal comprising a nucleotide sequence, encoding a CLN5 variant or derivative or homologue thereof, which variant comprises a mutation at amino acid 207 or functionally equivalent residue wherein said animal exhibits an altered phenotype relative to a wild type mammal.

(ii) a non-human mammal comprising a nucleotide sequence encoding a canine CLN5 variant or derivative or homologue thereof which variant comprises mutation at amino acid 207 or functionally equivalent residue wherein said mammal exhibits aberrant CLN5 functional activity.

(iii) a non-human mammal comprising a nucleotide sequence encoding a canine CLN5 variant or derivative or homologue thereof, which variant comprises an amino acid sequence with a deletion of glutamine 207 or functionally equivalent residue wherein said mammal exhibits aberrant CLN5 functional activity.

(iv) a non-human mammal comprising a nucleotide sequence encoding a canine CLN5 variant or derivative or homologue thereof, which variant comprises an amino acid sequence with a Gln207Stop substitution wherein said mammal exhibits aberrant CLN5 functional activity.

(v) a non-human mammal comprising a nucleotide sequence encoding a CLN5 variant or derivative or homologue thereof, which variant comprises an amino acid sequence which is truncated at glutamine 207 wherein said mammal exhibits a NCL phenotype.

(vi) a non-human mammal comprising a nucleotide sequence encoding an amino acid sequence substantially as set forth in SEQ ID NO:18 or a derivative or homologue thereof, or an amino acid sequence having at least 50%, 60%, 70%, 80%, 90%, 95%, 96%, 97%, 98%, 99% or more sequence identity to SEQ ID NO:18 over a region of 150, 160, 170, 180, 185, 190, 195, 200, 201, 202, 203, 204 or 205 residues of SEQ ID NO:18 wherein said mammal exhibits aberrant CLN5 functional activity.

(vii) a non-human mammal comprising a nucleotide sequence which sequence comprises a mutation at C619, or functionally equivalent residue or having at least about 50%, 60%, 70%, 80%, 90%, 95%, 96% 97%, 98%, 99% or more sequence identity over a region of 800, 850, 900, 950, 1000, 1010, 1020, 1030, 1040, 1045, 1050 or 1052 of said sequence wherein said mammal exhibits aberrant CLN5 functional activity.

(viii) a non-human mammal comprising a nucleotide sequence which sequence comprises a substitution at C619, or functionally equivalent residue or having at least about 50%, 60%, 70%, 80%, 90%, 95%, 96%, 97%, 98%, 99% or more sequence identity over a region of 800, 850, 900, 950, 1000, 1010, 1020, 1030, 1040, 1045, 1050 or 1052 of said sequence wherein said mammal exhibits aberrant CLN5 functional activity.

(ix) a non-human mammal comprising a nucleotide sequence which sequence comprises a C619T substitution, or functionally equivalent residue or having at least about 50%, 60%, 70%, 80%, 90%, 95%, 96%, 97%, 98%, 99% or more sequence identity over a region of 800, 850, 900, 950, 1000, 1010, 1020, 1030, 1040, 1045, 1050 or 1052 of said sequence wherein said mammal exhibits aberrant CLN5 functional activity.

(x) a non-human mammal comprising a nucleotide sequence encoding an expression product wherein said nucleotide sequence is substantially as set forth in SEQ ID NO:17 or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of SEQ ID NO:17 wherein said mammal exhibits aberrant a NCL phenotype.

(xi) a non-human mammal comprising a nucleotide sequence substantially as set forth in SEQ ID NO:17 wherein said mammal exhibits a NCL phenotype.

In a related aspect, there is provided a method for screening a mammal for the onset, predisposition to the onset or being a carrier of a disease characterised by aberrant CLN5 functioning and/or expression, said method comprising screening a biological sample derived from said mammal for one or more mutations in the CLN5 gene and/or protein wherein the expression of said mutation is indicative of the onset or predisposition to the onset of said condition or of said mammal being a carrier of said disease.

More particularly, there is provided a method for screening a mammal for the onset, predisposition to the onset or being a carrier of a lysosomal storage disease, said method comprising screening a biological sample derived from said mammal for one or more mutations in the CLN5 gene and/or protein wherein the expression of said mutation is indicative of the onset or predisposition to the onset of said condition or of said mammal being a carrier of said disease.

Still more particularly, there is provided a method for screening a mammal for the onset, predisposition to the onset or being a carrier of NCL, said method comprising screening a biological sample derived from said mammal for one or more mutations in the CLN5 gene and/or protein wherein the expression of said mutation is indicative of the onset or predisposition to the onset of said NCL, or of said mammal being a carrier of said NCL.

In another aspect, there is provided a method for screening a mammal for the onset, predisposition to the onset or being a carrier of NCL, said method comprising screening a biological sample derived from said mammal for one or more mutations in the CLN5 gene, which mutation is a mutation of C619 or functionally equivalent residue, wherein the expression of said mutation is indicative of the onset or predisposition to the onset of said NCL or of said mammal being a carrier of said NCL.

In yet another aspect there is provided a method for screening a mammal for the onset, predisposition to the onset or being a carrier of NCL, said method comprising screening a biological sample derived from said mammal for one or more mutations in the CLN5 expression product, which mutation is a mutation of glutamine 207 or functionally equivalent residue, wherein the expression of said mutation is indicative of the onset or predisposition to the onset of said NCL or of said mammal being a carrier of said NCL.

In still another aspect there is provided a method for screening a canine for the onset, predisposition to the onset or being a carrier of NCL, said method comprising screening a biological sample derived from said canine for one or more mutations in the CLN5 gene, which mutation is a mutation of C619 or functionally equivalent residue, wherein the expression of said mutation is indicative of the onset or predisposition to the onset of said NCL or of said canine being a carrier of said NCL.

In still yet another aspect there is provided a method for screening a canine for the onset, predisposition to the onset or being a carrier of NCL, said method comprising screening a biological sample derived from said canine for one or more mutations in the CLN5 expression product, which mutation is a mutation of glutamine 207 or functionally equivalent residue, wherein the expression of said mutation is indicative of the onset or predisposition to the onset of said NCL or of said mammal being a carrier of said NCL.

Yet another aspect of the present invention is directed to a method for screening for an agent capable of modulating variant polypeptide CLN5 functional activity or variant CLN5 gene expression, said method comprising contacting a putative modulatory agent with a cell, or cell extract thereof, comprising a variant CLN5 nucleic acid molecule, as hereinbefore defined, and detecting an altered expression phenotype.

In still yet another aspect the present invention is directed to a method for screening for an agent capable of modulating the NCL phenotype in a mammal, said method comprising administering to a mammal expressing a variant CLN5 nuclei acid molecule a putative modulatory agent and detecting an altered expression phenotype.

Yet still another aspect of the present invention provides a method for screening for an agent capable of modulating variant polypeptide CLN5 functional activity and/or variant CLN5 gene expression in a mammal, said method comprising contacting one or more mutant non-human mammals, as hereinbefore defined, with one or more putative modulatory agents and determining whether said agent alters a variant CLN5 mediated phenotype.

Still another aspect of the present invention is directed to antibodies to CLN5 polypeptide and nucleic acid variants as hereinbefore defined.

Another aspect of the present invention contemplates a method of modulating variant CLN5 functional activity or the expression of a variant CLN5 nucleic acid sequence in a mammal, said method comprising administering to said mammal an effective amount of a modulatory agent for a time and under conditions sufficient to modulate at least one functional activity of said variant polypeptide or the expression of said nucleic acid molecule.

Still another aspect of the present invention relates to the treatment and/or prophylaxis of a condition in a mammal, which condition is characterised by aberrant CLN5 functional activity, said method comprising administering to said mammal an effective amount of a modulatory agent for a time and under conditions sufficient to modulate said aberrant CLN5 functional activity.

Yet another further aspect of the present invention provides a method for the treatment and/or prophylaxis of NCL, said method comprising administering to said mammal an effective amount of a modulatory agent of the present invention for a time and under conditions sufficient to ameliorate one or more symptoms characteristic of said NCL.

A further aspect of the present invention relates to the use of a modulatory agent in the manufacture of a medicament for the modulation of aberrant CLN5 functional activity or expression and/or the treatment of a condition characterised by aberrant CLN5 functional activity.

In yet another further aspect the present invention contemplates a composition comprising a modulatory agent as hereinbefore defined together, optionally, with one or more pharmaceutically acceptable carriers and/or diluents.

BRIEF DESCRIPTION OF THE DRAWINGS

FIG. 2 is a schematic representation of the sequence (SEQ ID NO:3) and predicted translation (SEQ ID NO:4) of CLN5 exon 4 region in Border collie with site of transition to T in NCL variant highlighted as a white letter on black background. Primer A (SEQ ID NO:12) and Primer B (SEQ ID NO:16) were used for restriction fragment length polymorphism detection and Primer A (SEQ ID NO:11) and Primer C (SEQ ID NO:15) for sequencing. MseI restriction sites are indicated by underlined sequence, with the dashed underline indicating the MseI site present only in the disease allele.

FIG. 4 is a graphical representation of the alignment of the predicted human (SEQ ID NO:5), mouse (SEQ ID NO:6), pig (SEQ ID NO:7), and dog (SEQ ID NO:8) CLN5 polypeptides. The canine CLN5 sequence was determined from consensus of Border collie sequences and the boxer and poodle genomes. Amino acids identical in three or more sequences are highlighted with black background, while gray background indicates similar residues. Positions of known mutations in humans (Savukoski et al. 1998, supra) and dogs are indicated as "h" and "d", respectively.

DETAILED DESCRIPTION OF THE INVENTION

Figure 1:
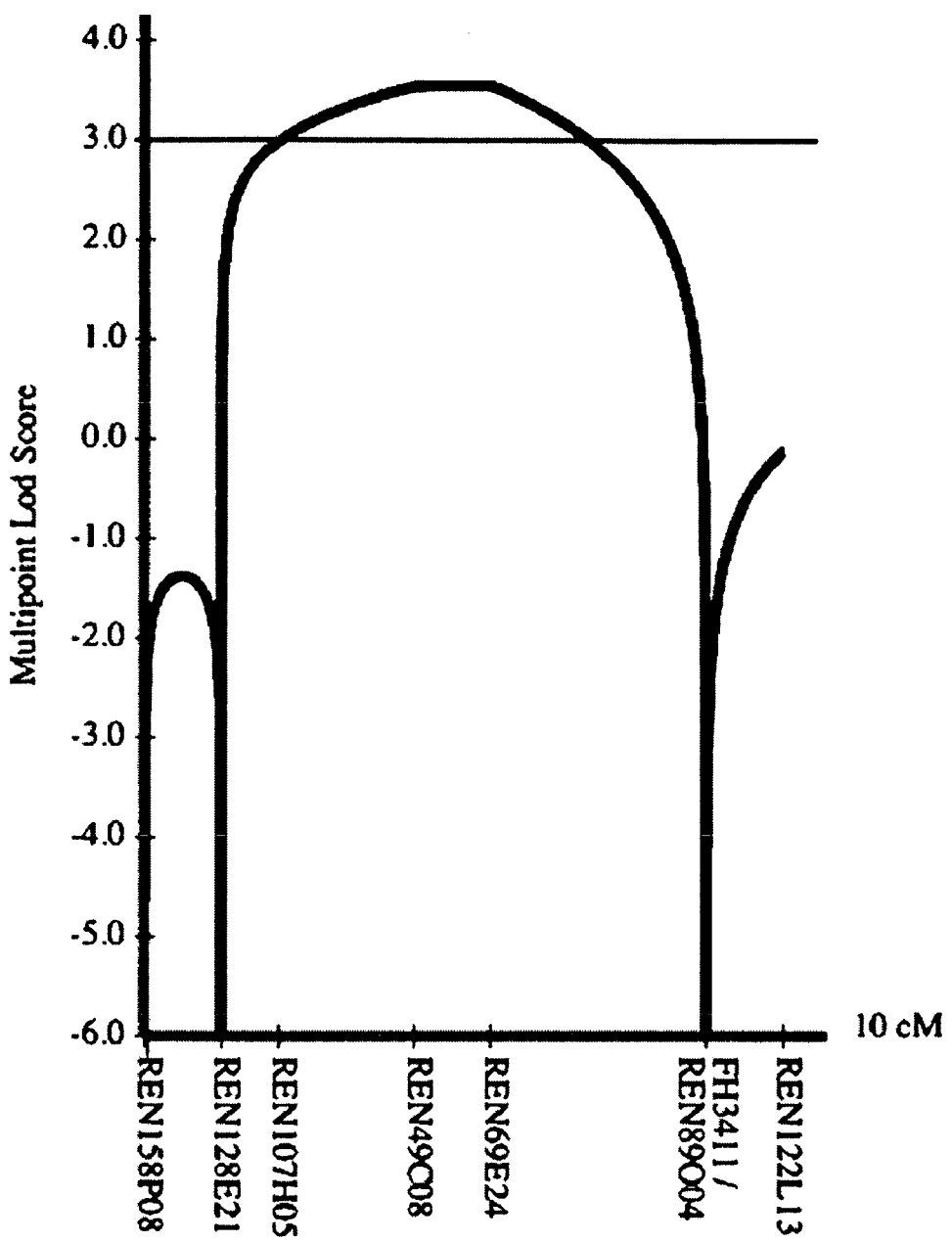
FIG. 1 is a graphical representation of the lod scores from multipoint linkage analysis of eight markers on CFA22 for linkage to Border collie NCL in 10 pedigrees. The position of the markers was determined from the dog genome sequence V1.1.

The present invention is predicated, in part, on the determination that a single nucleotide point mutation in the fourth exon of the nucleic acid sequence encoding canine CLN5 results in the production of a variant soluble lysosomal glycoprotein, specifically CLN5, which exhibits aberrant functional activity. In animals expressing this variant form of CLN5, a significantly higher incidence is observed of susceptibility to the onset of NCL. These determinations have now facilitated the development of diagnostic methods directed to assessing the onset or predisposition to the onset of disease conditions characterised by the expression of a variant CLN5 gene. Also facilitated are CLN5 DNA and protein variants and uses thereof. Still further, there are provided both in vivo and in vitro based screening means for identifying modulators of the functioning of this protein or expression of the variant gene and their application both therapeutically and prophylactically.

Accordingly, one aspect of the present invention is directed to a CLN5 protein variant comprising a mutation at amino acid 207 or functionally equivalent residue wherein said variant exhibits altered functional activity relative to wild-type CLN5 or a derivative, homologue or analogue of said CLN5 variant.

Another aspect of the present invention is directed to a canine CLN5 protein variant comprising a mutation at amino acid 207 or functionally equivalent residue wherein said variant exhibits altered functional activity relative to wild-type CLN5 or a derivative, homologue or analogue of said CLN5 variant.

Reference to "CLN5" (ceroid lipfuscinosis protein 5) should be understood as including reference to all forms of canine CLN5 or functional derivatives or homologues or analogues thereof. Without limiting the present invention to any one theory or mode of action, the canine CLN5 protein corresponds to a 350 amino acid soluble lysosomal glycoprotein which is thought to function by, inter alia, interacting directly with CLN2 and CLN3. It does not exhibit homology with any other NCL proteins. In humans, it has been shown to be expressed in embryonic human brain at the beginning of cortical neurogenesis and its expression is increased as cortical development proceeds. CLN5 is highly conserved between humans and mice, with the exception of the first exon. To date, four disease forming mutations have been recorded in human CLN5.

Reference to "CLN5" should be understood to include reference to all protein forms of CLN5 including, for example, any isoforms which arise from alternative splicing of CLN5 mRNA or allelic or polymorphic variants of CLN5.

Reference to CLN5 "functional activity" should be understood as a reference to any one or more of the activities which CLN5 performs. Without limiting the present invention in any way, and as detailed hereinbefore, CLN5 is thought to interact with CLN2 and CLN3. However, the variant form of CLN5 which is disclosed herein terminates prematurely. Specifically the C619T mutation of SEQ ID NO: 1 results in the translation of an expression product where the glutamine at position 207 of SEQ ID NO: 2 is substituted with a translation stop point, resulting in the generation of a 207 aa expression product rather than a 350 aa expression product. The truncated canine CLN5 protein exhibits extremely aberrant functional activity, as do the human CLN5 truncation mutations which are known to cause NCL in children. In a preferred embodiment, the subject altered functional activity is aberrant functioning linked to premature truncation of the CLN5 protein. Even more particularly, the subject functional activity is the inability of CLN5 to interact normally with CLN2 and/or CLN3. To this end, reference to "aberrant CLN5 functional activity" should be understood as a reference to activity which is altered relative to that which is characteristic of wild type CLN5.

The term "protein" should be understood to encompass peptides, polypeptides and proteins. It should also be understood that these terms are used interchangeably herein. The protein may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "protein" includes a protein comprising a sequence of amino acids as well as a protein associated with other molecules such as amino acids, lipids, carbohydrates or other peptides, polypeptides or proteins.

Reference to "mutation" and "mutant" and "variant" are terms which are used interchangeably and should be understood as a reference to any change, alteration or other modification, whether occurring naturally or non-naturally, which results in a CLN5 molecule exhibiting functionally altered activity relative the activity of wild-type CLN5.

In accordance with this preferred embodiment there is provided a canine CLN 5 protein variant comprising an amino acid sequence with a deletion of Glutamine 207 or functionally equivalent residue wherein said variant exhibits altered functional activity relative to wild-type CLN5 or a derivative, homologue or analogue of said CLN5 variant.

More specifically, said amino acid deletion corresponds to Gln 207 stop, this resulting in truncation of the variant CLN5 expression product at residue 207.

Truncation "at" residue 207 should be understood to mean that residue 206 is retained in the translated expression product and that truncation of the protein occurs between residues 206 and 207.

Still more particularly, said altered functional activity is activity which is aberrant due to truncation of the CLN5 expression product.

Most particularly, said canine CLN5 is a Border Collie CLN5.

In terms of the present invention, reference to "wild-type" CLN5 is a reference to the forms of CLN5 expressed by most animals in a given canine population wherein the subject CLN5 exhibits normal functional activity, for example normal interaction with CLN2 and CLN3, within the context discussed hereinbefore. There may be greater than one wild-type form of CLN5 (for example due to allelic or isoform variation) and the level or nature of functional activity exhibited by said wild-type CLN5 molecules may fall within a range of levels. However, it should be understood that "wild-type" does not include reference to a naturally occurring form of CLN5 which is not fully functionally active.

Reference to a "functionally equivalent" residue should be understood as a reference to a corresponding residue in other forms of CLN5. For example, other allelic or homologous forms of CLN5, for example, may exhibit minor differences in sequence length or structure. To this end, the exon 4 C residue which is located at position 619 of SEQ ID NO: 1 (Border Collie CLN5) may occur at a different position in CLN5 of other canines or other Border Collie forms of CLN5. Accordingly, it should be understood that the present invention extends to mutations at these corresponding positions. It would be well within the skill of the person in the art to assess any form of CLN5, in terms of a sequence alignment analysis, to determine the position and nature of the nucleic acid residue which corresponds to the C residue at position 619 of SEQ ID NO: 1.

The present invention is intended to extend to CLN5 variants, such as CLN5 homologue variants, which exhibit a mutation in a functionally equivalent region, thereby resulting in a corresponding functional outcome.

The CLN5 variant molecule exemplified in the present application corresponds to a Border Collie CLN5 variant. However, it should be understood that the present invention is not intended to be limited in this regard and extends to CLN5 variant homologues from other mammalian species, in particular other canines. In the context of Border Collie CLN5, it has been determined that Border Collies expressing one allele of the exemplified CLN5 variant are carriers of NCL or susceptible to the onset of NCL, while Border Collies expressing this mutation in both CLN5 alleles are subject to the onset of NCL, the onset of this phenotype being thought to be due to a reduced capacity of the truncated CLN5 to interact with CLN2 or CLN3. The exemplified CLN5 variant exhibits truncation of the expression product at amino acid 207 due to substitution of cytosine with thymine at position 619 of the encoding gene, resulting in the substitution of a caa glutamine codon for a "taa" stop codon, which codon is located in exon 4 of the CLN5 gene. In this regard, SEQ ID NO: 1 is a cDNA sequence corresponding to exons 1, 2, 3 and 4 of the wild type Border Collie CLN5 gene. SEQ ID NO: 2 shows the wild type CLN5 expression product. SEQ ID NO: 17 shows the Border Collie CLN5 cDNA in its mutated form while SEQ ID NO: 18 shows the expression product produced by SEQ ID NO: 17.

The present invention therefore preferably provides a canine CLN5 protein variant comprising an amino acid truncation at Glutamine 207, or functionally equivalent residue, wherein said variant exhibits aberrant functional activity relative to wild type CLN5 or a derivative, homologue or analog of said CLN5 variant.

In a related aspect, the present invention provides:

(i) isolated polypeptides comprising an amino acid sequent substantially as set forth in SEQ ID NO:18 or a polypeptide comprising an amino acid sequence having at least 50%, 60%, 70%, 80%, 90%, 95%, 96%, 97%, 98%, 99% or more sequence identity to SEQ ID NO:18 over a region of 150, 160, 170, 180, 185, 190, 195, 200, 201, 202, 203, 204 or 205 residues or a derivative, homologue or analogue thereof.

(ii) isolated or recombinant polypeptides encoded by a nucleotide sequence as hereinafter described.

Preferably, the subject polypeptide exhibits altered functional activity relative to wild-type CLN5 and, even more preferably, aberrant functional activity due to premature truncation of CLN5.

The protein of the present invention is preferably in isolated form. By "isolated" is meant a protein having undergone at least one purification step and this is conveniently defined, for example, by a composition comprising at least about 10% subject protein, preferably at least about 20%, more preferably at least about 30%, still more preferably at least about 40-50%, even still more preferably at least about 60-70%, yet even still more preferably 80-90% or greater of subject protein relative to other components as determined by molecular weight, amino acid sequence or other convenient means. The protein of the present invention may also be considered, in a preferred embodiment, to be biologically pure.

As used herein, in terms of both the claimed proteins and nucleic acid molecules, the term "isolated" means that the material is removed from its original environment (e.g., the natural environment if it is naturally occurring). For example, a naturally occurring polynucleotide or protein present in a living animal is not isolated, but the same polynucleotide or protein, separated from some or all of the coexisting materials in the natural system, is isolated. Such polynucleotides could be part of a vector and/or such polynucleotides or protein could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

Proteins of the invention can be isolated from natural sources, be synthetic, or be recombinantly generated polypeptides. Peptides and proteins can be recombinantly expressed in vitro or in vivo. The proteins of the invention can be made and isolated using any method known in the art. Proteins of the invention can also be synthesized, whole or in part, using chemical methods well known in the art. See e.g., Caruthers (1980) *Nucleic Acids Res. Symp. Ser.* 215-223; Horn (1980) *Nucleic Acids Res. Symp. Ser.* 225-232; Banga, A. K., *Therapeutic Peptides and Proteins, Formulation, Processing and Delivery Systems* (1995) Technomic Publishing Co., Lancaster, Pa. For example, peptide synthesis can be performed using various solid-phase techniques (see e.g., Roberge (1995) Science 269:202; Merrifield (1997) *Methods Enzymol.* 289:3-13) and automated synthesis may be achieved, e.g., using the ABI 431A Peptide Synthesizer (Perkin Elmer) in accordance with the instructions provided by the manufacturer.

"Derivatives" include fragments, parts and portions, from natural, synthetic or recombinant sources including fusion proteins. Parts or fragments include, for example, active regions of CLN5. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins.

A "homologue" refers to a sequence (nucleotide or protein) in another animal or organism which has at least about 60% identity to the reference sequence. A preferred homologue is a canine homologue.

The derivatives include fragments having particular epitopes or parts of the entire protein fused to peptides, polypeptides or other proteinaceous or non-proteinaceous molecules.

Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Derivatives of nucleic acid sequences may similarly be derived from single or multiple nucleotide substitutions, deletions and/or additions including fusion with other nucleic acid molecules. The derivatives of the nucleic acid molecules of the present invention include oligonucleotides, PCR primers, antisense molecules, molecules suitable for use in cosuppression and fusion of nucleic acid molecules. Derivatives of nucleic acid sequences also include degenerate variants.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl--aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |

TABLE 2-continued

| Non-conventional amino acid | Code | Non-conventional amino acid | Code |
|---|---|---|---|
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

Preferably, said derivatives, homologues and analogues are functional derivatives, homologues and analogues.

The proteins of the invention, as defined above, include all "mimetic" and "peptidomimetic" forms. The terms "mimetic" and "peptidomimetic" refer to a synthetic chemical compound which has substantially the same structural and/or functional characteristics of the proteins of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with proteins of the invention which are conservative variants, routine experimentation will determine whether a mimetic is within the scope of the invention, i.e., that its structure and/or function is not substantially altered.

Protein mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide Backbone Modifications," Marcell Dekker, NY).

A protein can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thienylalanine; D- or L-1, -2, 3-, or 4-pyrenylalanine; D- or L-3 thienylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; K- or L-p-methoxy-biphenylphenylalanine; D- or L-2-indole(alkyl)alanines; and, D- or L1-alkylalinines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3(2-morpholinyl-(4-ethyl)carbodiimide or 1-ethyl-3(4-azonia-4,4-dimethylpentyl)carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a protein of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but which can additionally be referred to as the R- or S-form.

The invention also provides proteins that are "substantially identical" to an exemplary protein of the invention. A "substantially identical" amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine).

The skilled artisan will recognize that individual synthetic residues and proteins incorporating these mimetics can be synthesized using a variety of procedures and methodologies, which are well described in the scientific and patent literature, e.g., Organic Syntheses Collective Volumes, Gilman, et al. (Eds) John Wiley & Sons, Inc., NY. Peptides and peptide mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) *Mol. Biolechnol.* 9:205-223; Hruby (1997) *Curr. Opin. Chem. Biol.* 1:114-119; Ostergaard (1997) *Mol. Divers.* 3:17-27; Ostresh (1996) *Methods Enzymol.* 267:220-234. Modified peptides of the invention can be further produced by chemical modification methods, see, e.g., Belousov (1997) *Nucleic Acids Res.* 25:3440-3444; Frenkel (1995) *Free Radic. Biol. Med.* 19:373-380; Blommers (1994) *Biochemistry* 33:7886-7896.

Proteins of the invention can also be synthesised and expressed as fusion proteins with one or more additional domains linked thereto for, e.g., to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising protein to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Purif.* 12:404-14). The histidine residues facilitate detection and purification while the enterokinase cleavage site provides a means for purifying a region from the remainder of the fusion protein. Technology pertaining to vectors encoding fusion proteins and application of fusion proteins are well described in the scientific and patent literature, see e.g., Kroll (1993) *DNA Cell. Biol.*, 12:441-53.

To the extent that the present invention relates to CLN5 variants, and in particular CLN5 variants comprising truncation at amino acid 206 of SEQ ID NO: 2, it should also be understood to extend to nucleic acid molecules encoding said variants.

Accordingly, another aspect of the present invention is directed to an isolated nucleic acid molecule selected from the list consisting of:

(i) An isolated nucleic acid molecule or derivative, homologue or analogue thereof comprising a nucleotide sequence encoding or complementary to a sequence encoding a CLN5 variant or derivative or homologue of said variant which variant comprises a mutation at amino acid 207 or functionally equivalent residue wherein said variant exhibits altered functional activity relative to wild-type CLN5.

(ii) An isolated nucleic acid molecule or derivative, homologue or analogue thereof comprising a nucleotide sequence encoding or complementary to a sequence encoding a canine CLN5 variant or derivative or homologue of said variant which variant comprises a mutation at amino acid 207 or functionally equivalent residue wherein said variant exhibits altered functional activity relative to wild-type CLN5.

(iii) An isolated nucleic acid molecule or derivative, homologue or analogue thereof comprising a nucleotide sequence encoding or complementary to a sequence encoding a canine CLN5 variant or derivative or homologue of said variant which variant comprises an amino acid sequence with a deletion of glutamine 207 or functionally equivalent residue wherein said variant exhibits altered functional activity relative to wild-type CLN5.

(iv) An isolated nucleic acid molecule or derivative, homologue or analogue thereof comprising a nucleotide sequence encoding or complementary to a sequence encoding a canine CLN5 variant or derivative or homologue of said variant which variant comprises an amino acid sequence with Gln 207 stop wherein said variant exhibits altered functional activity relative to wild-type CLN5.

(v) An isolated nucleic acid molecule or derivative, homologue or analogue thereof comprising a nucleotide sequence encoding or complementary to a sequence encoding a canine CLN5 variant or derivative or homologue of said variant, which variant comprises an amino acid sequence which is truncated at glutamine 207, or functionally equivalent region, of SEQ ID NO: 2 wherein said variant exhibits altered functional activity relative to wild-type CLN5.

(vi) An isolated nucleic acid molecule or derivative, homologue or analogue thereof comprising a nucleotide sequence, or a sequence complementary to said sequence, which sequence comprises a mutation at canine CLN5 C619, or functionally equivalent residue, or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of said sequence and/or is capable of hybridising to said sequence under low stringency conditions at 42° C.

(vii) An isolated nucleic acid molecule or derivative, homologue or analogue thereof comprising a nucleotide sequence, or a sequence complementary to said sequence, which sequence comprises a substitution at canine CLN5 C619, or functionally equivalent residue, or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of said sequence and/or is capable of hybridising to said sequence under low stringency conditions at 42° C.

(viii) An isolated nucleic acid molecule or derivative, homologue or analogue thereof comprising a nucleotide sequence, or a sequence complementary to said sequence, which sequence comprises a canine CLN5 C619T substitution, or functionally equivalent residue, or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of said sequence and/or is capable of hybridising to said sequence under low stringency conditions at 42° C.

(ix) An isolated nucleic acid molecule or derivative, homologue or analogue thereof comprising a nucleotide sequence encoding, or complementary to a sequence, encoding an amino acid sequence substantially as set forth in SEQ ID NO:18 or a derivative or homologue thereof, or an amino acid sequence having at least 50%, 60%, 70%, 80%, 90%, 95%. 96%, 97%, 98%, 99% or more sequence identity to SEQ ID NO:18 over a region of 150, 160, 170, 180, 185, 190, 195, 200, 201, 202, 203, 204 or 205 residues of SEQ ID NO:18 and/or is capable of hybridizing to said nucleic acid molecule under low stringency conditions at 42° C.

(x) An isolated nucleic acid molecule or derivative, homologue or analogue thereof comprising a nucleotide sequence encoding, or complementary to a sequence, wherein said nucleotide sequence is substantially as set forth in SEQ ID NO:17 or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1030, 1040, 1045, 1050, or 1052 residues of SEQ ID NO:17 and/or is capable of hybridising to SEQ ID NO:17 or complementary form thereof under low stringency conditions at 42° C.

(xi) An isolated nucleic acid molecule or derivative, homologue or analogue thereof comprising a nucleotide sequence as set forth in SEQ ID NO:17.

The present invention should be understood to extend to the genomic DNA form of the nucleotide sequences detailed above.

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) *Toxicol. Appl. Pharmacol.* 144:189-197; Strauss-Soukup (1997) *Biochemistry* 36:8692-8698; Samstag (1996) *Antisense Nucleic Acid Drug Dev* 6:153-156.

An "expression product" includes an RNA molecule such as an mRNA transcript as well as a protein. Some genes are non-protein encoding genes and produce mRNA or other RNA molecules and are involved in regulation by RNA:DNA, RNA:RNA or RNA:protein interaction. The RNA (e.g. mRNA) may act directly or via the induction of other molecules such as RNAi or via products mediated from splicing events (e.g. exons or introns). Short, interfering RNA (siRNA) is also contemplated by the present invention. Other genes encode mRNA transcripts which are then translated into proteins. A protein includes a polypeptide. The differentially expressed nucleic acid molecules, therefore, may encode mRNAs only or, in addition, proteins. Both mRNAs and proteins are forms of "expression products".

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) *J. Am. Chem. Soc.* 105:661; Belousov (1997) *Nucleic Acids Res.* 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; U.S. Pat. No. 4,458,066.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which may be chemically synthesized.

Techniques for the manipulation of nucleic acids, such as, e.g., subcloning, labelling probes (e.g., random-primer labelling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabelling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The invention provides expression vectors and cloning vehicles comprising nucleic acids of the invention, e.g., sequences encoding the proteins of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, *Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair.

The invention provides libraries of expression vectors encoding polypeptides and peptides of the invention. These nucleic acids may be introduced into a genome or into the cytoplasm or a nucleus of a cell and expressed by a variety of conventional techniques, well described in the scientific and patent literature. See, e.g., Roberts (1987) *Nature* 328:731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids of the invention are administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids of the invention; and may be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) *J. Virol.* 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The term "expression cassette" as used herein refers to a nucleotide sequence which is capable of affecting expression of a structural gene (i.e., a protein coding sequence, such as a polypeptide of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. "Operably linked" as used herein refers to linkage of a promoter upstream from a DNA sequence such that the promoter mediates transcription of the DNA sequence. Thus, expression cassettes also include plasmids, expression vectors, recombinant viruses, any form of recombinant "naked DNA" vector, and the like.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and includes both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The invention also provides a transformed cell comprising a nucleic acid sequence of the invention, e.g., a sequence encoding a polypeptide or the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

The vector may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes; incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL1650).

For transient expression of the protein-encoding DNA, for example, COS-1 cells may be transfected with approximately 8 μg DNA per 106 COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of 5×106 cells/dish and then grown for 24 hours in FBS-supplemented DMEM/F12 medium. Medium is then removed and cells are washed in PBS and then in medium. A transfection solution containing DEAE dextran (0.4 mg/ml), 100 μM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of 5×105 in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

In practicing the invention, nucleic acids encoding the polypeptides of the invention, or modified nucleic acids, can be reproduced by, e.g., amplification. The invention provides amplification primer sequence pairs for amplifying nucleic acids encoding polypeptides of the invention, e.g., primer pairs capable of amplifying nucleic acid sequences comprising the exemplary SEQ ID NO:1 or SEQ ID NO:17, or subsequences thereof.

Amplification methods include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) *Genomics* 4:560; Landegren (1988) *Science* 241:1077; Barringer (1990) *Gene* 89:117); transcription amplification (see, e.g., Kwoh (1989) *Proc. Natl. Acad. Sci. USA* 86:1173); and, self-sustained sequence replication (see, e.g., Guatelli (1990) *Proc. Natl. Acad. Sci. USA* 87:1874); Q Beta replicase amplification (see, e.g., Smith (1997) *J. Clin. Microbiol.* 35:1477-1491), automated Q-beta replicase amplification assay (see, e.g., Burg (1996) *Mol. Cell Probes* 10:257-271) and other RNA polymerase mediated techniques (e.g., NASBA, Cangene, Mississauga, Ontario); see also Berger (1987) *Methods Enzymol.* 152:307-316; Sambrook; Ausubel; U.S. Pat. Nos. 4,683,195 and 4,683,202; Sooknanan (1995) *Biotechnology* 13:563-564.

Reference herein to similarity or identity is generally at a level of comparison of at least 15 consecutive or substantially consecutive nucleotides or amino acids. It is particularly convenient, however, to determine similarity by comparing a total or complete sequence, after optimal alignment.

The term "similarity" as used herein includes exact identity between compared sequences at the nucleotide or amino acid level. Where there is non-identity at the nucleotide level, "similarity" includes differences between sequences which may encode different amino acids that are nevertheless related to each other at the structural, functional, biochemical and/or conformational levels. In a particularly preferred embodiment, nucleotide sequence comparisons are made at the level of identity rather than similarity.

Terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25: 3389, 1997). A detailed discussion of sequence analysis can be found in Unit 19.3 of Ausubel et al. ("Current Protocols in Molecular Biology" John Wiley & Sons Inc, Chapter 15, 1994-1998). A range of other algorithms may be used to compare the nucleotide and amino acid sequences such as but not limited to PILEUP, CLUSTALW, SEQUENCHER or VectorNTI.

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

As detailed above, and more specifically, protein and/or nucleic acid sequence identities (homologies) may be evaluated using any of the variety of sequence comparison algorithms and programs known in the art. The extent of sequence identity (homology) may be determined using any computer program and associated parameters, including those described herein, such as BLAST 2.2.2. or FASTA version 3.0t78, with the default parameters. For example, the sequence comparison algorithm is a BLAST version algorithm. In one aspect, for nucleic acid sequence identity analysis, the BLAST nucleotide parameters comprise word size=11, expect=10, filter low complexity with DUST, cost to open gap=5, cost to extend gap=2, penalty for mismatch=−3, reward for match=1, Dropoff (X) for BLAST extensions in bits=20, final X dropoff value for gapped alignment=50, and all other options are set to default. In one aspect, for polypeptide sequence identity analysis the sequence comparison algorithm is a BLAST version algorithm, e.g., where the BLAST nucleotide parameters comprise word size=3, expect=10, filter low complexity with SEG, cost to open gap=11, cost to extend gap=1, similarity matrix Blosum62, Dropoff (X) for blast extensions in bits=7, X dropoff value for gapped alignment (in bits)=15, final X dropoff value for gapped alignment=25.

Exemplary algorithms and programs include, but are not limited to, TBLASTN, BLASTP, FASTA, TFASTA, and CLUSTALW (Pearson and Lipman, *Proc. Natl. Acad. Sci. USA* 85(8):2444-2448, 1988; Altschul et al., *J. Mol. Biol.* 215(3):403-410, 1990; Thompson et al., *Nucleic Acids Res.* 22(2):4673-4680, 1994; Higgins et al., *Methods Enzymol.* 266:383-402, 1996; Altschul et al., *J. Mol. Biol.* 215(3):403-410, 1990; Altschul et al., *Nature Genetics* 3:266-272, 1993). Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications.

BLAST, BLAST 2.0 and BLAST 2.2.2 algorithms are also used to practice the invention. They are described, e.g., in; Altschul (1990) *J. Mol. Biol.* 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighbourhood word score threshold (Altschul (1990) supra). These initial neighbourhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) *Proc. Natl. Acad. Sci. USA* 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) *Proc. Natl. Acad. Sci. USA* 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blast. There are about 38 setting options in the BLAST 2.2.2 program. In this exemplary aspect of the invention, all default values are used except for the default filtering setting (i.e., all parameters set to default except filtering which is set to OFF); in its place a "-F F" setting is used, which disables filtering. Use of default filtering often results in Karlin-Altschul violations due to short length of sequence.

The default values used in this exemplary aspect of the invention include:

"Filter for low complexity: ON
Word Size: 3
Matrix: Blosum62
Gap Costs: Existence: 11
Extension: 1"

Other default settings are: filter for low complexity OFF, word size of 3 for protein, BLOSUM62 matrix, gap existence penalty of −11 and a gap extension penalty of −1.

The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, that sequence is within the scope of the invention.

The phrase "substantially identical" in the context of two nucleic acids or polypeptides, can refer to two or more sequences that have, e.g., at least about at least 90%, 91%, 92%, 93%, 94%, 95%, 96%, 97%, 98%, 99% or more sequence identity or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention. Nucleic acid sequences of the invention can be substantially identical over the entire length of a polypeptide coding region.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

As used herein, the terms "computer," "computer program" and "processor" are used in their broadest general contexts and incorporate all such devices.

The invention provides isolated or recombinant nucleic acids that hybridize under stringent conditions to an exemplary sequence of the invention. In alternative aspects, the stringent conditions are highly stringent conditions, medium stringent conditions or low stringent conditions, as known in the art and as described herein. These methods may be used to isolate nucleic acids of the invention.

In alternative aspects, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800 or more residues in length, or, the full length of a gene or coding sequence, e.g., cDNA. Nucleic acids shorter than full length are also included. These nucleic acids can be useful as, e.g., hybridization probes, labelling probes, PCR oligonucleotide probes, iRNA, antisense or sequences encoding antibody binding peptides (epitopes), motifs, active sites and the like.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m$=69.3+0.41 (G+C)% (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Where nucleic acids of the invention are defined by their ability to hybridize under high stringency, these conditions comprise about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

As detailed hereinbefore, the nucleotide sequence or amino acid sequence of the present invention may correspond to exactly the same sequence of the naturally occurring genomic gene (or corresponding cDNA) or protein or other expression product or may carry one or more nucleotide or amino acid substitutions, additions and/or deletions. Reference to "nucleic acid molecule" or "gene" includes, where appropriate, reference to the genomic gene or cDNA as well as any naturally occurring or induced derivatives. Apart from the substitutions, deletions and/or additions to the nucleotide sequence, the present invention further encompasses fragments, parts and portions of the disclosed nucleotide sequences.

Identification of CLN5 orthologs in other species can be performed using a number of methods known to those of skill in the art. These methods include computational genomic annotation, using programs such as BLAST and GeneScan (see, e.g., Lynn et al., J. Genet. 80: 9-16 (2001)); and biochemical methods, e.g., low stringency hybridization methods. For computational identification, BLAST version 2.0 is preferably used with parameters set at word size=3, expect=10, filter low complexity with SEG, cost to open gap=11, cost to extend gap=1, similarity matrix Blosum62, Dropoff (X) for blast extensions in bits=7, X dropoff value for gapped alignment (in bits)=15, final X dropoff value for gapped alignment=25.

In addition, one may isolate the genes encoding the novel polypeptides using methods known to the skilled artisan. For example, cDNA encoding a protein of interest may be identified by screening a cDNA library that can be obtained as an EcoRI-based lambda phage library (lambda ZAP) from Stratagene Cloning Systems (La Jolla, Calif., U.S.A.). The cDNA library may be screened, for example, using a plurality of random oligonucleotide probes constructed based on the known amino acid sequence obtained from a protein of interest using mass spectrometry. Exemplary conditions for screening comprise 6 times SSC, 25% formamide, 5% Dernhardt's solution, 0.5% SDS, 100 µg/ml denatured salmon sperm DNA, at 42° C. Exemplary processing of such screens comprise the following steps: filters are washed with 2 times SSC containing 0.5% SDS at 25° C. for 5 minutes, followed by a 15 minute wash at 50° C. with 2 times SSC containing 0.5% SDS; the final wash is with 1 times SSC containing 0.5% SDS at 50° C. for 15 minutes; filters are exposed to X-ray film (Kodak) overnight; of 106 clones screened, cDNA inserts are identified. The sequences of identified cDNAs may be determined, for example, by purifying plaques containing the cDNAs identified, and excising as phagemids according to the supplier's specifications, to generate insert-carrying Bluescript-SK variants of the phagemid vectors. Sequencing of the relevant clones across their entire sequence should reveal a putative ATG initiation codon together with an oligonucleotide of 5' non-coding region and the coding region having a polyA splice site.

Once CLN5 nucleic acids and/or polypeptides have been identified, mutations in these sequences can be readily identified by comparison to these wild type sequences. DNA and polypeptide sequencing methods are well known to those of skill in the art. As noted above, a mutated CLN5 polypeptide refers to a polypeptide that exhibits a deficiency in one or more characteristics displayed by wild type CLN5 proteins, such as amino acid truncation. Preferred mutated CLN5 polypeptides exhibit a detectable phenotypic effect when expressed in cells or animals. Particularly preferred mutated CLN5 polypeptides produce a NCL phenotype in animals or secrete functionally aberrant CLN5.

Mutations generated spontaneously may be identified by phenotypic effects that are known to relate to CLN5 function (e.g., NCL phenotypes seen with the CLN5 variant), and confirmed by direct sequencing of the putative mutant; by chromosome mapping; or by a combination of these methods. As an alternative to identifying spontaneous mutations in CLN5 sequences (for example, in terms of diagnostic applications, as detailed hereafter), methods for introducing mutations into a known wild type CLN5 sequence can be performed (for example, to create in vitro or in vivo models for further analysis). Such methods include site specific mutagenesis, in which a change in a nucleic acid sequence is introduced at a predetermined location in the sequence, and the nucleic acid is then introduced into a cell; gene transfer methods, in which a gene transfer vector is used to introduce a desired nucleic acid sequence into a cell genome; and "knockout" and "knockin" methods, in which a nucleic acid sequence is introduced into the genome of a cell at a specific location, often substituting an introduced gene for a genomic version (see, e.g., Kuhn, *Science* 269: 1427-9 (1995)). For example, in one embodiment it may be desirable to create a transgenic mouse which expresses the mutated canine CLN5 gene, such that a small animal model is provided for the study of canine NCL.

Methods for introducing or inducing mutations can be advantageously combined with nuclear transfer cloning methods to provide an animal comprising a mutated sequence of interest, e.g., by transferring the genetic material from a cell harboring the mutated sequence, preferably an embryonic stem cell in mice, into an enucleated oocyte; or with methods of blastocyst injection of genetically altered embryonic stem cells to provide germline chimeras; or with methods of pronuclear injection of fertilized mouse eggs with DNA constructs. See, e.g., Rideout et al., *Cell* 109: 17-27 (2002); Rideout et al., *Nat. Genet.* 24: 109-10 (2000); Nakao et al., *Exp. Anim.* 47:167-71 (1998). Alternatively, ENU can be used to mutagenize premeiotic spermatogonial stem cells in male animals, allowing the production of a large number of F1 founder animals from a single treated male.

Accordingly, a related aspect of the present invention provided non-human mammals comprising the subject CLN5 variant gene. The development of such transgenic animals facilitates the screening for and analysis of therapeutically and/or prophylactically effective proteinaceous or non-proteinaceous molecules which modulate the variant CLN5 expression or functioning and/or modulate the onset and progression of the NCL phenotype in animals expressing the CLN5 variant. This development now provides an extremely valuable means for, inter alia, rationally designing prophylactic and/or therapeutic treatment regimes.

Accordingly, another aspect of the present invention is directed to a non-human mammal comprising a CLN5 nucleic acid molecule variant wherein said mammal is characterised by an aberrant CLN5 functional activity phenotype.

The term "phenotype" should be understood as a reference to the totality of the functional and structural characteristics, or any particular characteristic or set of characteristics, of an animal as determined by interaction of the genotype of the organism with the environment in which it exists. In the context of the present invention, the subject phenotype is preferably aberrant CLN5 functional activity. In another preferred embodiment, said phenotype is the onset of NCL, a predisposition to the onset of NCL or the onset/predisposition to the onset of one or more symptoms associated with NCL. Accordingly, reference to an "NCL phenotype" should be understood as a reference to an animal with the onset of NCL, predisposition to the onset of NCL or one that is a carrier of NCL.

More particularly, the present invention is directed to a non-human mammal comprising a CLN5 nucleic acid molecule variant wherein said mammal is characterised by the onset or predisposition to the onset of, one or more symptoms of NCL or is a carrier of NCL.

Preferably, said mammal is characterised by the onset of an NCL phenotype.

Reference to "mammal", "CLN5" and "functional activity" should be understood to have the same meaning as hereinbefore provided.

There is therefore most preferably provided a non-human mammal selected from the list:

(i) a non-human mammal comprising a nucleotide sequence, encoding a CLN5 variant or derivative or homologue thereof, which variant comprises a mutation at amino acid 207 or functionally equivalent residue wherein said animal exhibits an altered phenotype relative to a wild type mammal.

(ii) a non-human mammal comprising a nucleotide sequence encoding a canine CLN5 variant or derivative or homologue thereof which variant comprises mutation at amino acid 207 or functionally equivalent residue wherein said mammal exhibits aberrant CLN5 functional activity.

(iii) a non-human mammal comprising a nucleotide sequence encoding a canine CLN5 variant or derivative or homologue thereof, which variant comprises an amino acid sequence with a deletion of glutamine 207 or functionally equivalent residue wherein said mammal exhibits aberrant CLN5 functional activity.

(iv) a non-human mammal comprising a nucleotide sequence encoding a canine CLN5 variant or derivative or homologue thereof, which variant comprises an amino acid sequence with a Gln207Stop substitution wherein said mammal exhibits aberrant CLN5 functional activity.

(v) a non-human mammal comprising a nucleotide sequence encoding a canine CLN5 variant or derivative or homologue thereof, which variant comprises an amino acid sequence which is truncated at glutamine 207 wherein said mammal exhibits a NCL phenotype.

(vi) a non-human mammal comprising a nucleotide sequence encoding an amino acid sequence substantially as set forth in SEQ ID NO:18 or a derivative or homologue thereof, or an amino acid sequence having at least 50%, 60%, 70%, 80%, 90%, 95%. 96%, 97%, 98%, 99% or more sequence identity to SEQ ID NO:18 over a region of 150, 160, 170, 180, 185, 190, 195, 200, 201, 202, 203, 204 or 205 residues of SEQ ID NO:18 wherein said mammal exhibits aberrant CLN5 functional activity.

(vii) a non-human mammal comprising a nucleotide sequence which sequence comprises a mutation at canine CLN5 C619, or functionally equivalent residue or having at least about 50%, 60%, 70%, 80%, 90%, 95%, 96%, 97%, 98%, 99% or more sequence identity over a region of 800, 850, 900, 950, 1000, 1010, 1020, 1030, 1040, 1045, 1050 or 1052 of said sequence wherein said mammal exhibits aberrant CLN5 functional activity.

(viii) a non-human mammal comprising a nucleotide sequence which sequence comprises a substitution at canine CLN5 C619, or functionally equivalent residue or having at least about 50%, 60%, 70%, 80%, 90%, 95%, 96%, 97%, 98%, 99% or more sequence identity over a region of 800, 850, 900, 950, 1000, 1010, 1020, 1030, 1040, 1045, 1050 or 1052 of said sequence wherein said mammal exhibits aberrant CLN5 functional activity.

(ix) a non-human mammal comprising a nucleotide sequence which sequence comprises a canine CLN5 C619T substitution, or functionally equivalent residue or having at least about 50%, 60%, 70%, 80%, 90%, 95%, 96%, 97%, 98%, 99% or more sequence identity over a region of 800, 850, 900, 950, 1000, 1010, 1020, 1030, 1040, 1045, 1050 or 1052 of said sequence wherein said mammal exhibits aberrant CLN5 functional activity.

(x) a non-human mammal comprising a nucleotide sequence encoding an expression product wherein said nucleotide sequence is substantially as set forth in SEQ ID NO:17 or a nucleotide sequence having at least about 50%, 60%, 70%, 80%, 90%, 95%, 96%, 97%, 98%, 99% or more identity over a region of at least about 800, 850, 900, 950, 1000, 1010, 1020, 1030, 1040, 1045, 1050 or 1052 residues of SEQ ID NO:17 wherein said mammal exhibits aberrant a NCL phenotype.

(xi) a non-human mammal comprising a nucleotide sequence substantially as set forth in SEQ ID NO:17 wherein said mammal exhibits a NCL phenotype.

Preferably, said non-human mammal is a dog or a mouse. Even more preferably, said aberrant CLN5 functional activity is aberrant oligomerisation and, still more preferably, a nerve degenerative disease phenotype.

It should be understood that the mammals of this aspect of the present invention may comprise any number of cells which comprise the nucleic acid molecule variant of the present invention. For example, to the extent that a mammal is mutagenised or transgenically generated, it may be expected that all the cells of the animal express a mutated genomic DNA sequence. Alternatively, in some situations perhaps only some of the cells of the mammal will express the variant nucleic acid molecule, such as where recombinantly modified cells are introduced, in a localised fashion (eg. into the central nervous system), to a subject mammal.

The coding sequences for the polypeptides to be expressed in the subject non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111, 166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) *J. Immunol. Methods* 231:147-157, describing the production of recombinant proteins in the milk of transgenic dairy animals; Baguisi (1999) *Nat. Biotechnol.* 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP). One exemplary method to produce genetically altered non-human animals is to genetically modify embryonic stem cells. The modified cells are injected into the blastocoel of a blastocyst. This is then grown in the uterus of a pseudopregnant female. In order to readily detect chimeric progeny, the blastocysts can be obtained from a different parental line than the embryonic stem cells. For example, the blastocysts and embryonic stem cells may be derived from parental lines with different hair color or other readily observable phenotype. The resulting chimeric animals can be bred in order to obtain non-chimeric animals which have received the modified genes through germ-line transmission. Techniques for the introduction of embryonic stem cells into blastocysts and the resulting generation of transgenic animals are well known.

Because cells contain more than one copy of a gene, the cell lines obtained from a first round of targeting are likely to be heterozygous for the targeted allele. In this particular context, the generation of heterozygous animals may of itself be useful in order to facilitate the further study of the heterozygous phenotype. Homozygosity, in which both alleles are modified, can be achieved in a number of ways. In one approach, a number of cells in which one copy has been modified are grown. They are then subjected to another round of targeting using a different selectable marker. Alternatively, homozygotes can be obtained by breeding animals heterozygous for the modified allele, according to traditional Mendelian genetics.

The identification of the variant CLN5 gene of the present invention is of particular importance due to the fact that it represents a previously unknown CLN5 mutation which is linked to the NCL phenotype. Accordingly, there is now provided an extremely valuable means of diagnosing both sufferers and carriers of NCL.

Accordingly, in a related aspect, there is provided a method for screening a mammal for the onset, predisposition to the onset or being a carrier of a disease characterised by aberrant CLN5 functioning and/or expression, said method comprising screening a biological sample derived from said mammal for one or more mutations in the CLN5 gene and/or protein wherein the expression of said mutation is indicative of the onset or predisposition to the onset of said condition or of said mammal being a carrier of said disease.

More particularly, there is provided a method for screening a mammal for the onset, predisposition to the onset or being a carrier of a lysosomal storage disease, said method comprising screening a biological sample derived from said mammal for one or more mutations in the CLN5 gene and/or protein wherein the expression of said mutation is indicative of the onset or predisposition to the onset of said condition or of said mammal being a carrier of said disease.

Reference to "CLN5 gene and/or protein" should be understood as a reference to the nucleic acid and protein molecules hereinbefore disclosed. Reference to "mutations" should similarly be understood as a reference to the CLN5 mutations hereinbefore disclosed.

Still more particularly, there is provided a method for screening a mammal for the onset, predisposition to the onset or being a carrier of NCL, said method comprising screening a biological sample derived from said mammal for one or more mutations in the CLN5 gene and/or protein wherein the expression of said mutation is indicative of the onset or predisposition to the onset of said NCL or of said mammal being a carrier of said NCL.

Reference to "NCL" should be understood as a reference to the autosomal recessive neurodegenerative disorders which are associated with the accumulation of lipofuscin in the brain. Specifically, in most cases subunit c of the mitochondrial ATP synthase accumulates except for the CLN1 mutation that results in the lipopigment containing high levels of saponins A and D (Tyynela el al. 1993, FEBS Letters 330:8-12). The ultrastructural patterns of these aggregates are variable and dependent on the gene mutated. These disorders are usually associated with severe outcomes including muscle incoordination, walking abnormalities or disturbances, blindness, mental retardation, seizures and early death. In humans, there are three main types of these diseases which are classified according to the age at which they begin—late infantile (Jansky-Bielschowsky), juvenile (Batten disease) and adult (Kufs or Pary's disease). The disorder may be evident at birth. More commonly it is diagnosed some time after the second year of life, in the teens, or as an adult. Later appearance of the disease in humans is associated with somewhat less severe disability while early onset is typically associated with a shortened life span.

The neuronal ceroid lipofuscinoses are collectively recognized as the most common neurodegenerative disorder in children. Mutations have been identified in six different genes (CLNs 1,2,3,5,6,8) that each result in a unique form of the disease that is distinguishable by the age of onset and clinical course (Mole 1999, *Lancet* 354:443-445). The Finnish variant (CLN5; vLINCL$_{Fin}$; MIM#256731) is a late infantile form of the disease, with a slower progression of symptoms than the classical late infantile form caused by a mutation of CLN2. Both of these forms of the disease exhibit a curvilinear ultrastructure pattern by electron microscopy, although the Finnish variant may also accumulate as fingerprints and rectilinear complexes (Santavuori et al. 1982, *Neuropediatrics* 13:135-141; Santavuori et al. 1999, The Neuronal Ceroid Lipofuscinoses (Batten disease). pp 91-101).

In Australian Border Collies this disease is fatal. Unfortunately, it is also quite widespread in the population due to the common use of some champion carrier dogs.

Without limiting the present invention in any way, NCL, has been identified in a range of animals including cow (Harper et al. 1988, supra), dog (Koppang 1973, supra), horse (Url et al. 2001, supra), and sheep (Jolly 1977, supra; Tyynela et al.), although only in a few cases have the genetic mutations been identified. Naturally occurring NCL mouse models exist for CLN6 (Bronson et al. 1998, supra) and CLN8 (Bronson et al. 1993, supra; Ranta et al. 1999, supra), while knockout and targeted disruption models exist for the other identified NCL genes (Mitchison et al. 1999, supra; Gupta et al. 2001, supra; Sleat et al. 2003, supra; Kopra et al. 2004, supra). A mutation in CLN6 has been identified as the cause of a late-onset form of NCL in sheep (Broom et al. 1999, supra). The first large animal model of CLN5 has been identified recently in Devon cattle in Australia (Houweling et al. 2004).

In a preferred embodiment, there is provided a method for screening a mammal for the onset, predisposition to the onset or being a carrier of NCL, said method comprising screening a biological sample derived from said mammal for one or more mutations in the CLN5 gene, which mutation is a mutation of C619 or functionally equivalent residue, wherein the expression of said mutation is indicative of the onset or predisposition to the onset of said NCL or of said mammal being a carrier of said NCL.

Preferably, said mutation is a C619 substitution and, most preferably, a C619T substitution.

In another preferred embodiment, there is provided a method for screening a mammal for the onset, predisposition to the onset or being a carrier of NCL, said method comprising screening a biological sample derived from said mammal for one or more mutations in the CLN5 expression product, which mutation is a mutation of glutamine 207 or functionally equivalent residue, wherein the expression of said mutation is indicative of the onset or predisposition to the onset of said NCL or of said mammal being a carrier of said NCL.

Preferably, said mutation is Gln207Stop and, still more preferably, truncation of the CLN5 expression product at residue 207.

In accordance with these preferred embodiments, said biological sample is a sample containing genomic DNA.

The preset invention is predicated on the finding that the expression of the CLN5 mutation disclosed herein occurs in subjects suffering from, predisposed to or carrying NCL. The occurrence of this mutation in the CLN5 gene in the context of one allele is indicative of a carrier of NCL while the occurrence of this mutation in both alleles is indicative of the onset or predisposition to the onset of NCL. NCL is an autosomal recessive condition. Accordingly, and without limiting the present invention in any way, if both parents carry the trait, the statistical likelihood is that:
(i) one of four offspring will have the disease
(ii) two of four offspring will be entirely normal but be carriers of the trait
(iii) one of four offspring will be entirely normal and not be a carrier.

Reference to "carrier" should therefore be understood as a reference to a subject who may not necessarily develop any of the symptoms of NCL but can nevertheless pass the mutation onto offspring such that their offspring may themselves become carriers or, if both parents carry the trait, may develop NCL. This is particularly important in the context of canines since a breeder dog which is actually a carrier of NCL will contribute to the ongoing and widespread propagation of NCL.

The person of skill in the art will understand that one may screen for changes to CLN5 levels at either the protein or the encoding nucleic acid molecule level. To the extent that it is not always specified, reference herein to screening for a mutation of "CLN5" should be understood to include reference to screening for either the CLN5 protein itself or its encoding primary RNA transcript, mRNA or genomic DNA.

Preferably, there is provided a method for screening a canine for the onset, predisposition to the onset or being a carrier of NCL, said method comprising screening a biological sample derived from said canine for one or more mutations in the CLN5 gene, which mutation is a mutation of C619 or functionally equivalent residue, wherein the expression of said mutation is indicative of the onset or predisposition to the onset of said NCL or of said canine being a carrier of said NCL.

Preferably, said mutation is a C619 substitution and, most preferably, a C619T substitution. More preferably, said canine is a Border Collie and said screening is performed on genomic DNA.

In another preferred embodiment, there is provided a method for screening a canine for the onset, predisposition to the onset or being a carrier of NCL, said method comprising screening a biological sample derived from said canine for one or more mutations in the CLN5 expression product, which mutation is a mutation of glutamine 207 or functionally equivalent residue, wherein the expression of said mutation is indicative of the onset or predisposition to the onset of said NCL or of said mammal being a carrier of said NCL. Preferably, said mutation is Gln207Stop and, still more preferably, truncation of the CLN5 expression product at residue 207. More preferably, said canine is a Border Collie.

Means of screening for mutations in the CLN5 gene and/or protein in an individual can be achieved by any suitable method, which would be well known to the person of skill in the art, such as but not limited to:
(i) In vivo detection of CLN5 protein. Molecular Imaging may be used following administration of imaging probes or reagents capable of disclosing altered CLN5 protein mRNA or protein expression product in the brain.
Molecular imaging (Moore et al., *BBA*, 1402:239-249, 1988; Weissleder et al., *Nature Medicine*, 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.

(ii) Analysis of mRNA expression in cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., W. *Clinical Chemistry* 48:9 1398-1405, 2002) or array technologies.
For example, a labelled polynucleotide encoding CLN5 variant protein may be utilized as a probe in a Northern blot of an RNA extract obtained from the brain, for example via a biopsy. Preferably, a nucleic acid extract from the subject is utilized in concert with oligonucleotide primers corresponding to sense and antisense sequences of a polynucleotide encoding CLN5 protein, or flanking sequences thereof, in a nucleic acid amplification reaction such as RT PCR, real time PCR or SAGE. A variety of automated solid-phase detection techniques are also appropriate. For example, a very large scale immobilized primer arrays (VLSIPS™) are used for the detection of nucleic acids as, for example, described by Fodor et al., 1991 and Kazal et al., 1996. The above genetic techniques are well known to persons skilled in the art.
For example, to detect CLN5 protein encoding RNA transcripts, RNA is isolated from a cellular sample suspected of containing CLN5 protein RNA. RNA can be isolated by methods known in the art, e.g. using TRIZOL™ reagent (GIBCO-BRL/Life Technologies, Gaithersburg, Md.). Oligo-dT, or random-sequence oligonucleotides, as well as sequence-specific oligonucleotides can be employed as a primer in a reverse transcriptase reaction to prepare first-strand cDNAs from the isolated RNA. Resultant first-strand cDNAs are then amplified with sequence-specific oligonucleotides in PCR reactions to yield an amplified product.
(iii) DNA amplification techniques provide a more sensitive means of screening for the presence of mutations in DNA extracted from a biological sample. They may be used for production of large amounts of amplified material which facilitates detection of a mutation by a detection technique or they may themselves be performed as a detection technique. Means of executing the amplification reactions and determining which reactions have resulted in the production of amplification product are well known to those skilled in the art. For example, primers can be designed to amplify specific regions of the DNA of interest. Depending on the design of a particular amplification reaction, the primer may be directed to achieving amplification of unmutated/normal sequence regions only or mutated sequence only. Accordingly, the interpretation to be attributed to the generation of amplification product will depend on whether the sequence which the primer is directed to amplify is the normal sequence or the mutated sequence. Where the sequence is the normal sequence, information is only provided in relation to the presence or absence of a mutated sequence. However, where the primer is directed to amplifying a mutated sequence, the specific nature of the mutation can be confirmed. In another example, an oligonucleotide ligation reaction can be designed such that ligation occurs or does not occur depending on whether the unmutated nucleotide or the mutation nucleotide is present in the DNA of interest, said occurrence or non-occurrence being determined by the nucleotide at the 3' end of the oligonucleotide which ligates to the 5' end of the other oligonucleotide. In still another example, one can design an extension reaction in which only some of the 4 nucleotides are available for incorporation into the extension product. In this scenario, it is the presence or absence of an extension product which will indicate the nature of the nucleotide which is present in the DNA region at the point where the primer extended. Various techniques can be used to analyse an amplification product for the presence of a mutation. Their operational characteristics, such as ease of use or sensitivity, vary so that different techniques may be useful for different purposes. They include but are not limited to:

Sequencing—for direct determination of the mutation

Pyrosequencing—for direct determination of the mutation

Enzyme digestion—an indirect technique based on the presence of the mutation leading to presence or loss of a restriction site or leading to facilitated cleavage of a DNA heteroduplex Microarray analysis which is based on the principle that DNA of interest hybridises or does not hybridise to different members of a panel of oligonucleotides depending on whether or not a mutation is present Denaturing gradient gel electrophoresis Denaturing high performance liquid chromatography Mass spectrometry Primer extension—a primer is designed to hybridise immediately adjacent to a mutation and the nucleotide (s) which is taken up to extend into the mutation is complementary to the mutation nucleotide(s). The taken-up nucleotide is colour labelled to facilitate detection of the extended primer Oligonucleotide-ligation. The oligonucleotide at the 3' end of the oligonucleotide which ligates to the 5' end of the second oligonucleotide is complementary to the mutated oligonucleotide at the residue of interest. The ligated product can be detected by an amplification reaction or by colour labelling one of the oligonucleotides followed by electrophoresis Mutation specific polymerase chain reaction. One of the primers is designed so that the oligonucleotide at the 3' end is complementary to the mutated oligonucleotide at the residue of interest.

Once an amplification product is generated, various techniques can be utilised to analyse that product, this being of particular relevance where more than one primer, directed to more than one mutation, was utilised. For example, in order to differentiate the amplification product resulting from the use of multiple primers, without the requirement to sequence the product, one can design primers which are of different length. This will result in the generation of amplification products which are of correspondingly different lengths. Where such products are electrophoresed, the amplification products of different length will run to different places on the gel, thereby facilitating either quantitative or qualitative analysis of the amount of product. This can be particularly important in the context of analysing biological samples which may comprise more than one mutated CLN5 gene. In another example, the nucleotides which form part of the amplification mixture, and are incorporated into the amplification product, can be colour coded. This is of particular relevance where primers are designed such that they hybridise immediately adjacent to a mutation and the nucleotides which are therefore taken up to extend the primer into the mutation are complementary to the mutation nucleotide sequence. Color-coding thereby enables one to visualise, without the need to sequence, precisely which nucleotides were taken up, thereby providing one with the sequence information in relation to the subject mutation. This includes methods that incorporate mismatches to CLN5 gene sequence within the primers so they are not completely complementary but still amplify the CLN5 gene.

(iv) Measurement of altered CLN5 protein in cell extracts or blood or other suitable biological sample, either qualitatively or quantitatively, for example by immunoassay, utilising immunointeractive molecules.

In one example, one may seek to detect variant CLN5 protein-immunointeractive molecule complex formation. For example, an antibody according to the invention, having a reporter molecule associated therewith, may be utilized in immunoassays. Such immunoassays include but are not limited to radioimmunoassays (RIAs), enzyme-linked immunosorbent assays (ELISAs) and immunochromatographic techniques (ICTs), Western blotting which are well known to those of skill in the art. For example, reference may be made to "Current Protocols in Immunology", 1994 which discloses a variety of immunoassays which may be used in accordance with the present invention. Immunoassays may include competitive assays. It will be understood that the present invention encompasses qualitative and quantitative immunoassays.

Suitable immunoassay techniques are described, for example, in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to a target antigen. The antigen in this case is variant CLN5 protein or a fragment thereof.

Two-site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilized on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well known in the art and generally consist of crosslinking covalently binding or physically adsorbing, the polymer-antibody complex is washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilized first antibody.

An alternative method involves immobilizing the antigen in the biological sample and then exposing the immobilized antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following:

(a) direct attachment of the reporter molecule to the antibody;
(b) indirect attachment of the reporter molecule to the antibody; i.e., attachment of the reporter molecule to another assay reagent which subsequently binds to the antibody; and
(c) attachment to a subsequent reaction product of the antibody.

The reporter molecule may be selected from a group including a chromogen, a catalyst, an enzyme, a fluorochrome, a chemiluminescent molecule, a paramagnetic ion, a lanthanide ion such as Europium ($Eu^{34}$), a radioisotope including other nuclear tags and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in U.S. Patent Nos. U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al., International Publication No. WO 93/06121. Reference also may be made to the fluorochromes described in U.S. Pat. No. 5,573,909 (Singer et al), U.S. Pat. No. 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodate. As will be readily recognized, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art and are particularly useful for the present method. However, other reporter molecules, such as radioisotope, chemiluminescent or bioluminescent molecules may also be employed.

(v) The use of aptamers in screening for nucleic acid molecules or expression products
(vi) Determining altered protein expression based on any suitable functional test, enzymatic test or immunological test in addition to those detailed in point (iii)-above.

As detailed above, any suitable technique may be utilised to detect variant CLN5 protein or its encoding nucleic acid molecule. The nature of the technique which is selected for use will largely determine the type of biological sample which is required for analysis. Such determinations are well within the scope of the person of skill in the art.

Preferably said variant nucleic acid molecule which is the subject of detection is genomic DNA and said screening technique is selected from:
(i) amplification
(ii) oligonucleotide ligation assay
(iii) direct sequence analysis
(iv) ligase chain reaction
(v) ligase detection reaction
(vi) PCR-based restriction fragment length polymorphism
(vii) Polyacrylamide gel electrophoresis
(viii) Pyrosequencing (ix) Single strand polymorphism assay
(x) DNA probing
(xi) Taq cycle sequencing
(xii) The invader assay
(xiii) TaqMan 5' nuclease assay Reference to a "biological sample" should be understood as a reference to any sample of biological material derived from an animal such as, but not limited to, cellular material, blood, faeces, tissue biopsy specimens or fluid which has been introduced into the body of an animal and subsequently removed (such as, for example, solution retrieved from an enema wash). The biological sample which is tested according to the method of the present invention may be tested directly or may require some form of treatment prior to testing. For example, a biopsy sample may require homogenisation prior to testing or it may require sectioning for in situ testing. Further, to the extent that the biological sample is not in liquid form, (if such form is required for testing) it may require the addition of a reagent, such as a buffer, to mobilise the sample.

To the extent that the target molecule is present in a biological sample, the biological sample may be directly tested or else all or some of the nucleic acid material present in the biological sample may be isolated prior to testing. In yet another example, the sample may be partially purified or otherwise enriched prior to analysis. For example, to the extent that a biological sample comprises a very diverse cell population, it may be desirable to select out a sub-population of particular interest if protein expression product or mRNA is the subject of analysis. It is within the scope of the present invention for the target nucleic acid molecule to be pre-treated prior to testing, for example, inactivation of live virus or being run on a gel. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation, such as the nature of the condition being monitored. Preferably, said sample is blood, buccal scrapes, saliva, stool or tissue sample.

The term "subject" to the extent that it is used herein includes canines, primates, livestock animals (e.g. horses, cattle, sheep, pigs, donkeys), laboratory test animals (e.g. mice, rats, rabbits, guinea pigs), companion animals (e.g. cats) and captive wild animals (e.g. kangaroos, deer, foxes). Preferably, the subject is a canine and, even more preferably, a Border Collie.

Another aspect of the present invention provides a diagnostic kit for use in accordance with the method of the present invention said kit comprising an agent for detecting one or more mutations in the CLN5 gene and/or protein, at least one of which mutations is a mutation of C619 or functionally equivalent residue of the CLN5 gene and/or a mutation of amino acid 207 or functionally equivalent residue of the CLN5 protein, and reagents useful for facilitating the detection of said agent. Further means may also be included, for example, to receive a biological sample. The agent may be an antibody or other suitable detection molecule.

As detailed hereinbefore, the present invention encompasses providing CLN5 gene variant function to a cell in either an in vitro or in vivo context. This is particularly useful when generating an animal model. A target gene or a part of the gene may be introduced into the cell in a vector such that the gene remains extrachromosomal. In such a situation, the gene will be expressed by the cell from the extrachromosomal location. If a gene portion is introduced and expressed in a cell carrying a mutant target allele, the gene portion should encode a part of the target protein. Vectors for introduction of genes both for recombination and for extrachromosomal maintenance are known in the art and any suitable vector may be used. Methods for introducing DNA into cells such as electroporation calcium phosphate co-precipitation and viral transduction are known in the art.

Gene transfer systems known in the art may be useful in the practice of genetic manipulation. These include viral and non-viral transfer methods. A number of viruses have been used as gene transfer vectors or as the basis for preparing gene transfer vectors, including papovaviruses (e.g. SV40, Madzak et al., *J. Gen. Virol.* 73: 1533-1536, 1992), adenovirus (Berkner, *Curr. Top. Microbiol. Immunol.* 158: 39-66, 1992; Berkner et al., BioTechniques 6, 616-629, 1988; Gorziglia and Kapikian, *J. Virol.* 66: 4407-4412, 1992; Quantin et al., *Proc. Natl. Acad. Sci. USA* 89: 2581-2584, 1992; Rosenfeld et al., *Cell* 68: 143-155, 1992; Wilkinson et al., *Nucleic Acids Res.* 20: 2233-2239, 1992; Stratford-Perricaudet et al., *Hum. Gene Ther.* 1: 241-256, 1990; Schneider et al., *Nature Genetics* 18: 180-183, 1998), vaccinia virus (Moss, *Curr. Top. Microbiol. Immunol.* 158: 25-38, 1992; Moss, *Proc. Natl. Acad. Sci. USA* 93: 11341-11348, 1996), adeno-associated virus (Muzyczka, *Curr. Top. Microbiol. Immunol.* 158: 97-129, 1992; Ohi et al., *Gene* 89: 279-282, 1990; Russell and Hirata, *Nature Genetics* 18: 323-328, 1998), herpesviruses including HSV and EBV (Margolskee, *Curr. Top., Microbiol. Immunol.* 158: 67-95, 1992; Johnson et al., *J. Virol.* 66: 2952-2965, 1992; Fink et al., *Hum. Gene Ther.* 3: 11-19, 1992; Breakefield and Geller, *Mol. Neurobiol.* 1: 339-371, 1987; Freese et al., *Biochem. Pharmacol.* 40: 2189-2199, 1990; Fink et al., *Ann. Rev. Neurosci.* 19: 265-287, 1996), lentiviruses (Naldini et al., *Science* 272: 263-267, 1996), Sindbis and Semliki Forest virus (Berglund et al., *Biotechnology* 11: 916-920, 1993) and retroviruses of avian (Bandyopadhyay and Temin, *Mol. Cell. Biol.* 4: 749-754, 1984; Petropoulos et al., *J. Viol.* 66: 3391-3397, 1992], murine [Miller, *Curr. Top. Microbiol. Immunol.* 158: 1-24, 1992; Miller et al., *Mol. Cell. Biol.* 5: 431-437, 1985; Sorge et al., *Mol. Cell. Biol.* 4: 1730-1737, 1984; and Baltimore, *J. Virol.* 54: 401-407, 1985; Miller et al., *J. Virol.* 62: 4337-4345, 1988] and human [Shimada et al. *J. Clin. Invest.* 88: 1043-1047, 1991; Helseth et al., *J. Virol.* 64: 2416-2420, 1990; Page et al., *J. Virol.* 64: 5270-5276, 1990; Buchschacher and Panganiban, *J. Virol.* 66: 2731-2739, 1982] origin.

Non-viral gene transfer methods are known in the art such as chemical techniques including calcium phosphate co-precipitation, mechanical techniques, for example, microinjection, membrane fusion-mediated transfer via liposomes and direct DNA uptake and receptor-mediated DNA transfer. Viral-mediated gene transfer can be combined with direct in vivo gene transfer using liposome delivery, allowing one to direct the viral vectors to particular cells. Alternatively, the retroviral vector producer cell line can be injected into particular tissue. Injection of producer cells would then provide a continuous source of vector particles.

In an approach which combines biological and physical gene transfer methods, plasmid DNA of any size is combined with a polylysine-conjugated antibody specific to the adenovirus hexon protein and the resulting complex is bound to an adenovirus vector. The trimolecular complex is then used to infect cells. The adenovirus vector permits efficient binding, internalization and degradation of the endosome before the coupled DNA is damaged. For other techniques for the delivery of adenovirus based vectors, see U.S. Pat. No. 5,691,198.

Liposome/DNA complexes have been shown to be capable of mediating direct in vivo gene transfer.

If the polynucleotide encodes a sense or antisense polynucleotide or a ribozyme or DNAzyme, expression will produce the sense or antisense polynucleotide or ribozyme or DNAzyme. Thus, in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

It should therefore be understood that the present invention also provides cells and cell lines comprising the nucleotide molecules described above, in the context of genetically modified non-human animals. These cells/cell lines may be derived from any suitable source, or may be generated by any suitable means, such as the means detailed hereinbefore. It should also be understood that to the extent that an isolated cell or an a cell located in an animal comprises the nucleic acid molecule variant of the present invention, that nucleic acid molecule variant may be naturally occurring, the result of a mutation event applied to the naturally occurring wild-type form of the nucleic acid molecule or it may have been recombinantly introduced. Each of these methods has been described in detail hereinbefore.

The development of the mammals and cells of the present invention now facilitates a wide variety of highly useful applications including, but not limited to:

(i) the production of proteins encoded by the nucleic acid molecule variants hereinbefore described
(ii) screening methods to identify modulators of variant CLN5 polypeptide functional activity or variant CLN5 gene expression
(iii) testing the effects of such modulators on aberrant CLN5 functional activity phenotypes, in particular the NCL phenotype.

Accordingly, yet another aspect of the present invention is directed to a method for screening for an agent capable of modulating variant polypeptide CLN5 functional activity or variant CLN5 gene expression, said method comprising contacting a putative modulatory agent with a cell, or cell extract thereof, comprising a variant CLN5 nucleic acid molecule, as hereinbefore defined, and detecting an altered expression phenotype.

It should be understood that the "cell" referenced in the context of this aspect of the present invention may be an isolated cell or population of cells, such as would be utilised in the context of an in vitro screening assay. Alternatively, the subject call may be one which is present in the non-human mammals hereinbefore described. This provides a basis for an in vivo screening method and is particularly useful, for example, where one is seeking to identify or test potential drugs in the context of their effect on the NCL phenotype, irrespective of the effect directly on variant CLN5 functioning. In this context, the Border Collie provides a highly useful large animal model for screening for or testing therapeutic or prophylactic protocols.

Accordingly, in still yet another aspect the present invention is directed to a method for screening for an agent capable of modulating the NCL phenotype in a mammal, said method comprising administering to a mammal expressing a variant CLN5 nucleic acid molecule a putative modulatory agent and detecting an altered expression phenotype.

Reference to a "modulatory agent" should be understood as a reference to any proteinaceous or non-proteinaceous molecule derived from natural, recombinant or synthetic sources including fusion proteins or following, for example, natural product screening and which achieves the object of the present invention. Synthetic sources of said agent include for example chemically synthesised molecules. In other examples, phage display libraries can be screened for peptides while chemical libraries can be screened for existing small molecules.

By way of example, diversity libraries, such as random combinatorial peptide or nonpeptide libraries can be screened. Many publically or commercially available libraries can be used such as chemically synthesized libraries, recombinant (e.g., phage display libraries) and in vitro translation-based libraries.

Examples of chemically synthesized libraries are described in Fodor et al., (1991); Houghten et al., (1991); Lam et al., (1991); Medynski., (1994); Gallop et al., (1994); Ohlmeyer et al., (1993); Erb et al., (1994); Houghten et al., (1992); Jayawickreme et al., (1994); Salmon et al., (1993); International Patent Publication No. WO 93/20242; and Brenner and Lerner., (1992).

Examples of phage display libraries are described by Scott and Smith., (1990); Devlin et al., (1990); Christian R. B et al., (1992); Lenstra., (1992); Kay et al., (1993) and International Patent Publication No. WO 94/18318.

In vitro translation-based libraries include but are not limited to those described in Mattheakis et al., (1994).

Without limiting the present invention in any way a test compound can be a macromolecule, such as biological polymer, including polypeptides, polysaccharides and nucleic acids. Compounds useful as potential therapeutic agents can be generated by methods well known to those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.,* 2:422-428 (1998); Tietze et al., *Curr. Biol.,* 2:363-381 (1998); Sofia, *Molecule. Divers.,* 3:75-94 (1998); Eichler et al., *Med. Res. Rev.* 15:481-496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37:1233-1251 (1994); Gordon et al., *J. Med. Chem.* 37:1385-1401 (1994); Gordon et al., *Acc. Chem. Res.* 29:144-154 (1996); Wilson and Czarnik, eds., *Combinatorial Chemistry: Synthesis and Application,* John Wiley & Sons, New York (1997).

Additionally, a test compound can be preselected based on a variety of criteria. For example, suitable test compounds having known modulating activity on a pathway suspected to be involved in a mutant CLN5 phenotype can be selected for testing in the screening methods. Alternatively, the test compounds can be selected randomly and tested by the screening methods of the present invention. Test compounds can be administered to the reaction system at a single concentration or, alternatively, at a range of concentrations from about 1 nM to 1 mM.

The number of different test compounds examined using the methods of the invention will depend on the application of the method. It is generally understood that the larger the number of candidate compounds, the greater the likelihood of identifying a compound having the desired activity in a screening assay. The methods can be performed in a single or multiple sample format. Large numbers of compounds can be processed in a high-throughput format which can be automated or semi-automated.

Reference to detecting an "altered expression phenotype" should be understood as the detection of any form of change associated with modulation of the variant CLN5 polypeptide activity or gene expression. These may be detectable, for example, as intracellular changes, changes observed extracellularly (for example, detecting changes in downstream product levels of activities) or changes in the phenotype/condition of a non-human mammalian subject. The type of change which one might screen for will largely depend on whether an in vivo or in vitro screening method is employed. Preferably, one is screening for changes which encompass the partial or full restoration of CLN5 functional activity.

In this regard, although this aspect of the present invention is directed to contacting a cell (either in an in vitro or in vivo context) with a putative modulatory agent, which cell comprises the CLN5 gene variant or derivative, homologue or analogue thereof as hereinbefore defined, in yet another related aspect, which is hereinafter discussed in more detail, the present invention extends to screening methods utilising the non-human animals of the present invention wherein the altered expression phenotype outcome which is screened for may not be due to direct modulation of the functional activity or expression of the CLN5 variant but may reflect the induction of an indirect modulation (i.e. the agent acts directly or indirectly on one or more unrelated molecules which thereafter act on the CLN5 expression product or gene) or the induction of an outcome, by means unrelated to CLN5 modulation, where the phenotypic outcome which is sought is achieved.

As detailed hereinbefore, screening for the modulatory agents hereinbefore defined can be achieved by any one of several suitable methods including, but in no way limited to, contacting a cell, in vitro, comprising the CLN5 variant nucleic acid molecule with an agent and screening for the modulation of CLN5 variant functional activity or modulation of the activity or expression of a downstream CLN5 functional outcomes. Detecting such modulation can be achieved utilising techniques such as Western blotting, electrophoretic mobility shift assays and/or the readout of reporters of CLN5 activity such as luciferases, CAT and the like.

Also as described in detail hereinbefore, it should be understood that the CLN5 variant protein expression may be naturally occurring in the cell which is the subject of testing or the genes encoding them may have been transfected into a host cell for the purpose of testing.

In another example, the subject of detection could be a downstream CLN5 target, rather than CLN5 itself. Yet another example includes CLN5 binding sites ligated to a minimal reporter. In alternative aspects, one may detect the amount of reporter gene transcript, the amount of polypeptide encoded by the reporter gene, or, where the reporter gene encodes an enzyme, detecting the amount of the enzyme's product or substrate, or, where the reporter gene encodes a bioluminescent protein, the luminescence of the protein. The reporter gene can encode any directly or indirectly detectable transcript or polypeptide.

As would be familiar to the skilled artisan, the expression of a target gene, or the modulation of expression of a target gene in vitro by a test compound, can be determined by measuring changes in expression. The methods of the invention involve measuring changes in gene expression by determining the amount of mRNA or polypeptide present in a sample. Methods for measuring both mRNA and polypeptide quantity are well known in the art. Methods for measuring mRNA typically involve detecting nucleic acid molecules by specific hybridization with a complementary probe in solution or solid phase formats.

Such methods include northern blots, polymerase chain reaction after reverse transcription of RNA (RT-PCR), and nuclease protection. Measurement of a response of a pathway component can be performed using large scale gene expression methods.

Large scale gene expression methods can be advantageously used to measure a large population of expressed genes in an organ, tissue or cell. Examples of methods well known in the art applicable to measuring a change in expression of a population of genes include cDNA sequencing, clone hybridization, differential display, subtractive hybridization, cDNA fragment fingerprinting, serial analysis of gene expression (SAGE), and DNA microarrays. These methods are useful, for example, for identifying differences in gene expression in an organ, tissue or cell of a mutant CLN5 non-human mammal compared to that of a wild type control animal.

A level of protein expression corresponding to a gene expression level also can be determined, in vitro, if desired. A variety of methods well known in the art can be used to determine protein levels either directly or indirectly. Such methods include immunochemical methods, such as western blotting, ELISA, immunoprecipitation, and RIA, gel electrophoresis methods including one and two-dimensional gels, methods based on protein or peptide chromatographic separation, methods that use protein-fusion reporter constructs and calorimetric readouts, methods based on characterization of activity translated polysomal mRNA, and mass spectrometric detection.

In practicing the screening methods of the invention, a test compound can be contacted with a polypeptide of the invention in vitro or administered to a cell of the invention or an animal of the invention in vivo. As discussed hereinbefore, combinatorial chemical libraries are one means to assist in the generation of new chemical leads compounds.

A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, the systematic, combinatorial mixing of 100 interchangeable chemical building blocks results in the theoretical synthesis of 100 million tetrameric compounds or 10 billion pentameric compounds (see, e.g., Gallop et al. (1994) 37(9): 1233-1250). Preparation and screening of combinatorial chemical libraries are well known to those of skill in the art, see, e.g., U.S. Pat. Nos. 6,004,617; 5,985,356. Such combinatorial chemical libraries include, but are not limited to, peptide libraries (see, e.g., U.S. Pat. No. 5,010, 175; Furka (1991) *Int. J. Pept. Prot. Res.,* 37: 487-493, Houghton et al. (1991) *Nature,* 354: 84-88). Other chemistries for generating chemical diversity libraries include, but are not limited to: peptoids (see, e.g., WO 91/19735), encoded peptides (see, e.g., WO 93/20242), random bio-oligomers (see, e.g., WO 92/00091), benzodiazepines (see, e.g., U.S. Pat. No. 5,288,514), diversomers such as hydantoins, benzodiazepines and dipeptides (see, e.g., Hobbs (1993) *Proc. Nat. Acad. Sci. USA* 90: 6909-6913), vinylogous polypeptides (see, e.g., Hagihara (1992) *J. Amer. Chem. Soc.* 114: 6568), non-peptidal peptidomimetics with a Beta-D-Glucose scaffolding (see, e.g., Hirschmann (1992) *J. Amer. Chem. Soc.* 114: 9217-9218), analogous organic syntheses of small compound libraries (see, e.g., Chen (1994) *J. Amer. Chem. Soc.* 116: 2661), oligocarbamates (see, e.g., Cho (1993) *Science* 261:1303), and/or peptidyl phosphonates (see, e.g., Campbell (1994) *J. Org. Chem.* 59: 658). See also Gordon (1994) *J. Med. Chem.* 37:1385; for nucleic acid libraries, peptide nucleic acid libraries, see, e.g., U.S. Pat. No. 5,539,083; for antibody libraries, see, e.g., Vaughn (1996) *Nature Biotechnology* 14:309-314; for carbohydrate libraries, see, e.g., Liang et al. (1996) *Science* 274: 1520-1522, U.S. Pat. No. 5,593,853; for small organic molecule libraries, see, e.g., for isoprenoids U.S. Pat. No. 5,569,588; for thiazolidinones and metathiazanones, U.S. Pat. No. 5,549,974; for pyrrolidines, U.S. Pat. Nos. 5,525,735 and 5,519,134; for morpholino compounds, U.S. Pat. No. 5,506,337; for benzodiazepines U.S. Pat. No. 5,288,514.

Devices for the preparation of combinatorial libraries are commercially available (see, e.g., U.S. Pat. Nos. 6,045,755; 5,792,431; 357 MPS, 390 MPS, Advanced Chem Tech, Louisville Ky., Symphony, Rainin. Woburn, Mass., 433A Applied Biosystems, Foster City, Calif., 9050 Plus, Millipore, Bedford, Mass.). A number of robotic systems have also been developed for solution phase chemistries. These systems include automated workstations, e.g., like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc. St. Louis, Mo., ChemStar, Ltd, Moscow, RU, 3D Pharmaceuticals, Exton, Pa., Martek Biosciences, Columbia, Md., etc.).

The present invention therefore preferably provides a method for screening for an agent capable of modulating variant polypeptide CLN5 functional activity and/or variant CLN5 gene expression in a mammal, said method comprising contacting one or more mutant non-human mammals, as hereinbefore defined, with one or more putative modulatory agents and determining whether said agent alters a variant CLN5 mediated phenotype.

Preferably said phenotype is NCL.

In a related aspect, one may also screen for the subject modulatory agents in in vitro based screening assays which do not rely on cellular expression of the variant CLN5 gene.

In practicing this aspect of the method of the invention, a variety of apparatus and methodologies can be used to in conjunction with the polypeptides and nucleic acids of the invention, e.g., to screen compounds as potential modulators (e.g., inhibitors or activators) of CLN5 variant activity, for antibodies that bind to a polypeptide of the invention, for nucleic acids that hybridize to a nucleic acid of the invention, to screen for cells expressing a polypeptide of the invention and the like.

In one aspect, the peptides and polypeptides of the invention can be bound to a solid support. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of peptides to a solid support can be direct (i.e., the protein contacts the solid support) or indirect (a particular compound or compounds are bound to the support and the target protein binds to this compound rather than the solid support). Peptides can be immobilized either covalently (e.g., utilizing single reactive thiol groups of cysteine residues (see, e.g., Colliuod (1993) *Bioconjugate Chem.* 4:528-536) or non-covalently but specifically (e.g., via immobilized antibodies (see, e.g., Schuhmann (1991) *Adv. Mater.* 3:388-391; Lu (1995) *Anal. Chem.* 67:83-87; the biotin/strepavidin system (see, e.g., Iwane (1997) *Biophys. Biochem. Res. Comm.* 230: 76-80); metal chelating, e.g., Langmuir-Blodgett films (see, e.g., Ng (1995) *Langmuir* 11:4048-55); metal-chelating self-assembled monolayers (see, e.g., Sigal (1996) *Anal. Chem.* 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl(4-iodoacetyl)aminobenzoate (SIAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon (1989) *Nature* 377:525-531 (1989).

The invention provides methods for identifying/screening for modulators (e.g., inhibitors, activators) of CLN5 variant activity, using arrays. Potential modulators, including small molecules, nucleic acids, polypeptides (including antibodies) can be immobilized to arrays. Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays can be used to simultaneously quantify a plurality of proteins. Small molecule arrays can be used to simultaneously analyze a plurality of CLN5 variant modulating or binding activities.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts. In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface.

Other identification methods include the yeast two-hybrid system in which CLN5 variant full-length polypeptide or fragments are expressed in yeast as "bait" fusion proteins in a screen against a cDNA library of "prey" fusion proteins. The fusion components of the screening system are typically the transactivation domain and DNA binding domain of a transcription factor such as yeast GAL4. When bait and prey bind each other, GAL4 transcriptional activation activity is reconstituted, upregulating transcription of a reporter gene construct. Such reporter constructs can be composed of GAL4 DNA binding sites upstream of a minimal promoter and marker gene such as lacZ, and library clones with increased reporter gene activity are identified by staining with β-D-galactoside.

Still another aspect of the present invention is directed to antibodies to CLN5 polypeptide and nucleic acid variants as hereinbefore defined. Such antibodies may be monoclonal or polyclonal and may be selected from naturally occurring antibodies or may be specifically raised. In the case of the latter, the CLN5 variant polypeptide or nucleic acid antigen may first need to be associated with a carrier molecule to achieve immunogenicity. The antibodies of the present invention are useful as therapeutic or diagnostic agents. An antibody "to" a molecule includes an antibody specific for said molecule.

These antibodies can be used to isolate, identify or quantify a polypeptide of the invention or related polypeptides.

The term "antibody" includes a peptide or polypeptide derived from, modelled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies to the molecules of the present invention may be monoclonal or polyclonal and may be selected from naturally occurring antibodies or may be specifically raised to these polypeptide and gene products. The present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool or as a means for purifying CLN5 polypeptide or nucleic acid variants.

Methods of immunization, producing and isolating antibodies (polyclonal and monoclonal) are known to those of skill in the art and described in the scientific and patent literature, see, e.g., Coligan, Current Protocols In Immunology, Wiley/Greene, NY (1991); Stites (eds.) Basic And Clinical Immunology (7th ed.) Lange Medical Publications, Los Altos, Calif. ("Stites"); Goding, Monoclonal Antibodies: Principles And Practice (2d ed.) Academic Press, New York, N.Y. (1986); Kohler (1975) Nature 256:495; Harlow (1988) Antibodies, A Laboratory Manual, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Identification of the CLN5 nucleic acid molecule variant which encodes a CLN5 variant polypeptide exhibiting aberrant functional activity, and therefore the capacity to screen for modulatory agents as hereinbefore described in detail, now provides molecules for use in the prophylactic and therapeutic treatment of diseases characterised by aberrant CLN5 functioning. Examples of diseases involving aberrant CLN5 functioning include, but are not limited to, NCL. Accordingly, the present invention contemplates therapeutic and prophylactic uses of said modulatory agents for the regulation of variant CLN5 polypeptide functional activity and/or nucleic acid expression or normalisation of the disease phenotype. In this regard, reference hereinafter to "modulatory agents" should be understood as a reference to:

(i) the agents identified by the various screening methodologies hereinbefore described;
(ii) the antibody molecules hereinbefore described.

Accordingly, another aspect of the present invention contemplates a method of modulating variant CLN5 functional activity or the expression of a variant CLN5 nucleic acid sequence in a mammal, said method comprising administering to said mammal an effective amount of a modulatory agent for a time and under conditions sufficient to modulate at least one functional activity of said variant polypeptide or the expression of said nucleic acid molecule.

Preferably, said modulation of functional activity is upregulation of the capacity of said variant CLN5 polypeptide to interact with downstream molecules, such as CLN2, in a normalised fashion.

Reference to "modulating" the subject functional activity or expression is a reference to up-regulating, down-regulating or otherwise altering one or more of the activities which characterise variant CLN5 activity or its expression.

Administration of the modulatory agent, in the form of a pharmaceutical composition, may be performed by any convenient means. The pharmaceutical composition is contemplated to exhibit therapeutic activity when administered in an amount which depends on the particular case. The variation depends, for example, on the human or animal and the sphingosine kinase or agent chosen. A broad range of doses may be applicable. Considering a patient, for example, from about 0.1 mg to about 1 mg of sphingosine kinase or agent may be administered per kilogram of body weight per day. Dosage regimes may be adjusted to provide the optimum therapeutic response. For example, several divided doses may be administered daily, weekly, monthly or other suitable time intervals or the dose may be proportionally reduced as indicated by the exigencies of the situation. The agent may be administered in a convenient manner such as by the oral, intravenous (where water soluble), intranasal, intraperitoneal, intramuscular, subcutaneous, intradermal or suppository routes or implanting (e.g. using slow release molecules). With particular reference to use of agents, these molecules may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

A further aspect of the present invention relates to the use of the invention in relation to mammalian disease conditions. For example, the present invention is particularly useful, but in no way limited to, use in therapeutically or prophylactically treating NCL.

Accordingly, another aspect of the present invention relates to the treatment and/or prophylaxis of a condition in a mammal, which condition is characterised by aberrant CLN5 functional activity, said method comprising administering to said mammal an effective amount of a modulatory agent for a time and under conditions sufficient to modulate said aberrant CLN5 functional activity.

Preferably, said condition is NCL.

According to this most preferred embodiment there is provided a method for the treatment and/or prophylaxis of NCL, said method comprising administering to said mammal an effective amount of a modulatory agent of the present invention for a time and under conditions sufficient to ameliorate one or more symptoms characteristic of said NCL.

The subject of the treatment or prophylaxis is generally a mammal such as but not limited to canine, livestock animal (eg. sheep, cow, horse, donkey, pig), companion animal (eg. cat), laboratory test animal (eg. mouse, rabbit, rat, guinea pig hamster), captive wild animal (eg. fox, deer). Preferably the mammal is a canine. Most preferably the mammal is a Border Collie.

Reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis including amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

An "effective amount" means an amount necessary at least partly to attain the desired response, or to delay the onset or inhibit progression or halt altogether, the onset or progression of a particular condition of the individual to be treated, the taxonomic group of individual to be treated, the degree of protection desired, the formulation of the vaccine, the assessment of the medical situation, and other relevant factors. It is expected that the amount will fall in a relatively broad range that can be determined through routine trials.

A further aspect of the present invention relates to the use of a modulatory agent in the manufacture of a medicament for the modulation of aberrant CLN5 functional activity or expression and/or the treatment of a condition characterised by aberrant CLN5 functional activity.

Preferably, said condition is NCL.

In accordance with these methods, the molecules defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

In yet another further aspect the present invention contemplates a composition comprising a modulatory agent as hereinbefore defined together, optionally, with one or more pharmaceutically acceptable carriers and/or diluents.

The invention provides compositions, in particular pharmaceutical compositions.

The modulatory agents of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

In one aspect, a solution of modulatory agents of the invention are dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration. The concentration of peptide in these formulations can vary widely, and will be selected primarily based on fluid volumes, viscosities, body weight and the like in accordance with the particular mode of administration selected and the patient's needs.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Modulatory agents of the invention, when administered orally, can be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix (1996) *Pharm Res.* 13:1760-1764; Samanen (1996) *J. Pharm. Pharmacol.* 48:119-135; U.S. Pat. No. 5,391,377, describing lipid compositions for oral delivery of therapeutic agents (liposomal delivery is discussed in further detail, infra).

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani (1996) "Systemic delivery of peptides and proteins across absorptive mucosae" *Crit. Rev. Ther. Drug Carrier Syst.* 13:85-184. For topical, transdermal administration, the agents are formulated into ointments, creams, salves, powders and gels. Transdermal delivery systems can also include, e.g., patches.

The modulatory agents of the invention can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention (see, e.g., Putney (1998) *Nat. Biotechnol.* 16:153-157).

For inhalation, the modulatory agents of the invention can be delivered using any system known in the art, including dry powder aerosols, liquids delivery systems, air jet nebulizers, propellant systems, and the like. See, e.g., Patton (1998) *Biotechniques* 16:141-143; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The modulatory agents of the invention can be delivered alone or as pharmaceutical compositions by any means known in the art, e.g., systemically, regionally, or locally (e.g., directly into, or directed to, a tumor); by intraarterial, intrathecal (IT), intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa). Actual methods for preparing administrable compositions will be known or apparent to those skilled in the art and are described in detail in the scientific and patent literature, see e.g., Remington's. For a "regional effect," e.g., to focus on a specific organ, one mode of administration includes intra-arterial or intrathecal (IT) injections, e.g., to focus on a specific organ, e.g., brain and CNS (see e.g., Gurun (1997) *Anesth Analg.* 85:317-323). For example, intra-carotid artery injection if preferred where it is desired to deliver a nucleic acid, peptide or polypeptide of the invention directly to the brain. Parenteral administration is a preferred route of delivery if a high systemic dosage is needed. Actual methods for preparing parenterally administrable compositions will be known or apparent to those skilled in the art and are described in detail, in e.g., Remington's. See also, Bai (1997) *J. Neuroimmunol.* 80:65-75; Warren (1997) *J. Neurol. Sci.* 152:31-38; Tonegawa (1997) *J. Exp. Med.* 186:507-515.

In one aspect, the pharmaceutical formulations comprising modulatory agents of the invention are incorporated in lipid monolayers or bilayers, e.g., liposomes, see, e.g., U.S. Pat. Nos. 6,110,490; 6,096,716; 5,283,185; 5,279,833. The invention also provides formulations in which water soluble modulatory agents of the invention have been attached to the surface of the monolayer or bilayer. For example, peptides can be attached to hydrazide-PEG-(distearoylphosphatidyl)ethanolamine-containing liposomes (see, e.g., Zalipsky (1995) *Bioconjug. Chem.* 6:705-708). Liposomes or any form of lipid membrane, such as planar lipid membranes or the cell membrane of an intact cell, e.g., a red blood cell, can be used. Liposomal formulations can be by any means, including administration intravenously, transdermally (see, e.g., Vutla (1996) *J. Pharm. Sci.* 85:5-8), transmucosally, or orally. The invention also provides pharmaceutical preparations in which the nucleic acid, peptides and/or polypeptides of the invention are incorporated within micelles and/or liposomes (see, e.g., Suntres (1994) *J. Pharm. Pharmacol.* 46:23-28; Woodle (1992) *Pharm. Res.* 9:260-265). Liposomes and liposomal formulations can be prepared according to standard methods and are also well known in the art, see, e.g., Remington's; Akimaru (1995) *Cytokines Mol. Ther.* 1:197-210; Alving (1995) *Immunol. Rev.* 145:5-31; Szoka (1980) *Ann. Rev. Biophys. Bioeng.* 9:467, U.S. Pat. Nos. 4,235,871, 4,501,728 and 4,837,028.

The pharmaceutical compositions of the invention can be administered in a variety of unit dosage forms depending upon the method of administration. Dosages for typical modulatory pharmaceutical compositions are well known to those of skill in the art. Such dosages are typically advisorial in nature and are adjusted depending on the particular therapeutic context, patient tolerance, etc. The amount of modulatory agent adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton (1997) "Bioavailability and transport of peptides and peptide drugs into the brain" *Peptides* 18:1431-1439; Langer (1990) *Science* 249:1527-1533.

The terms "compound", "active agent", "pharmacologically active agent", "medicament", "active" and "drug" are used interchangeably herein to refer to a chemical compound that induces a desired pharmacological and/or physiological effect. The terms also encompass pharmaceutically acceptable and pharmacologically active ingredients of those active agents specifically mentioned herein including but not limited to salts, esters, amides, prodrugs, active metabolites, analogs and the like. When the terms "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc. The term "compound" is not to be construed as a chemical compound only but extends to peptides, polypeptides and proteins as well as genetic molecules such as RNA, DNA and chemical analogs thereof. Reference to a "peptide", "polypeptide" or "protein" includes molecules with a polysaccharide or lipopolysaccharide component. The term "potentiator" is an example of a compound, active agent, pharmacologically active agent, medicament, active and drug which modulates the level of expression or level of activity of a nucleic acid molecule or its expression product.

The present invention extends to a genetic approach to up-regulating or down-regulating expression of a gene encoding a target. Generally, it is more convenient to use genetic means to induce gene silencing such as pre- or post-transcriptional gene silencing. However, the general techniques can be used to up-regulate expression such as by increasing gene copy numbers or antagonizing inhibitors of gene expression.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

Antisense polynucleotide sequences, for example, are useful in silencing transcripts of target genes. Expression of such an antisense construct within a cell interferes with target gene transcription and/or translation. Furthermore, co-suppression and mechanisms to induce RNAi or siRNA may also be employed. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example, Summerton and Weller, *Antisense and Nucleic Acid Drug Development* 7: 187-195, 1997). Such compounds are injected into embryos and the effect of interference with mRNA is observed.

In one embodiment, the present invention employs compounds such as oligonucleotides and similar species for use in modulating the function or effect of nucleic acid molecules such as those encoding a target, i.e. the oligonucleotides induce pre-transcriptional or post-transcriptional gene silencing. This is accomplished by providing oligonucleotides which specifically hybridize with one or more nucleic acid molecules encoding the target gene transcription. The oligonucleotides may be provided directly to a cell or generated within the cell. As used herein, the terms "target nucleic acid" and "nucleic acid molecule encoding a target gene transcript" have been used for convenience to encompass DNA encoding the target, RNA (including pre-mRNA and mRNA or portions thereof) transcribed from such DNA, and also cDNA derived from such RNA. The hybridization of a compound of the subject invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

"Complementary" as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

In the context of the subject invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

The open reading frame (ORF) or "coding region" which is known in the art to refer to the region between the translation initiation codon and the translation termination codon, is a region which may be effectively targeted. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns", which are excised from a transcript before it is translated. The remaining (and, therefore, translated) regions are known as "exons" and are spliced together to form a continuous mRNA sequence. Targeting splice sites, i.e. intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may, therefore, fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

In an alternative embodiment, genetic constructs including DNA vaccines are used to generate antisense molecules in vivo. Furthermore, many of the preferred features described above are appropriate for sense nucleic acid molecules or for gene therapy applications to promote levels of targets.

Following identification of an agent which potentiates or antagonizes a target, it may be manufactured and/or used in a preparation, i.e. in the manufacture or formulation or a composition such as a medicament, pharmaceutical composition or drug. These may be administered to individuals in a method of treatment or prophylaxis of infection. Alternatively, they may be incorporated into a patch or slow release capsule or implant.

In yet another aspect, the present invention provides kits comprising the compositions e.g. modulatory agents, expression cassettes, vectors, cells, antibodies, polypeptides, nucleic acid molecules etc. of the invention. The kits can also contain instructional material teaching the methodologies and uses of the invention, as described herein.

The present invention is further defined by the following non-limiting examples.

EXAMPLE 1

A Mutation in Canine CLN5 Causes Neuronal Ceroid Lipofuscinosis in Border Collie Dogs Results Linkage Analysis In five Border collie pedigrees segregating for NCL, two-point linkage analysis between the disease and microsatellite markers neighbouring the location of the canine homologue of CLN3 excluded this gene as the cause of Border collie NCL, and there was also a lack of support for linkage in the PPT1, TPP1 and CLN6 regions. Canine microsatellites were selected from the region of English setter NCL for multipoint linkage in nine Border collie pedigrees and yielded a maximum lod score of −4.6. This indicates that different genes were responsible for the diseases in the two breeds. Following the exclusion of these candidate disease loci, linkage to the disease was tested for the region on chromosome 22 containing CLN5 using the marker order determined by the dog genome sequence Build 1.1, which differs from the radiation hybrid map order (see Table 5). Using 10 pedigrees, a maximum lod score of 3.55 was obtained between microsatellite markers Ren128E21 and FH3441 on CFA22 (FIG. 1).

CLN5 Candidate Gene Analysis

A TBLASTN search at NCBI of the poodle dog genome (Kirkness et al. 2003, *Science* 301:1898-1903) (GenBank Accession No. AACN000000000) with the four exons of human CLN5 returned matches for exons 2, 3, and 4 (Table 6). Searches of the boxer genome (GenBank Accession No. AAEX00000000) with BLASTN revealed high homology matches in all four exons of human CLN5 (Table 6). No differences were observed between the predicted exon sequences of poodle and boxer and the sequences of Border collie exons 2, 3, and 4 for unaffected animals. Consensus sequences of these exons for affected and unaffected Border collies were submitted as GenBank Accession Nos. AY885121, AY885122, and AY885123.

Figure 3:
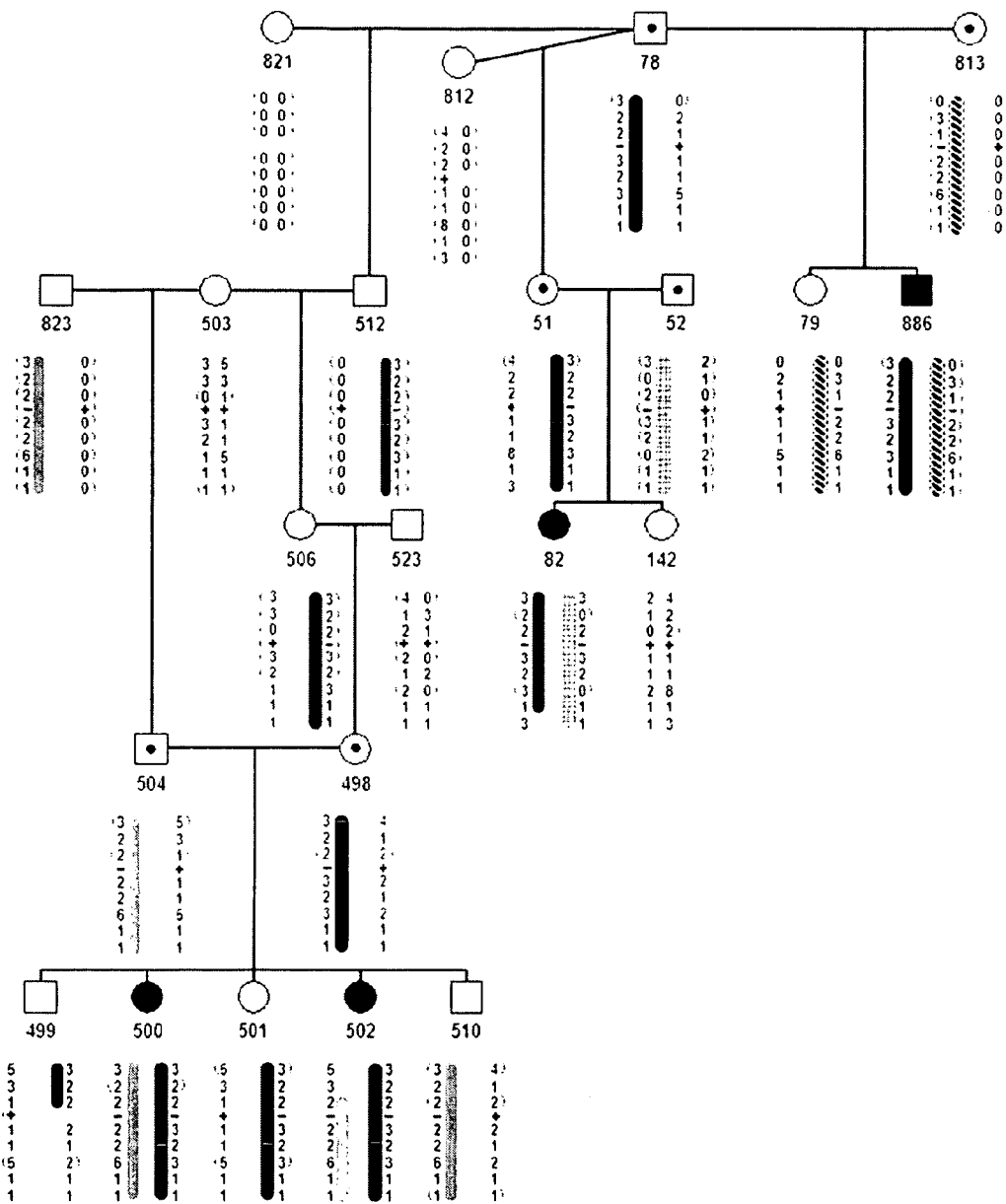
FIG. 3 is a schematic representation of a representative pedigree displaying segregation of the CLN5 mutation in Border collies. Solid symbols represent affected individuals, and known carriers of NCL are marked by dots. Some individuals used to determine linkage phase are not shown. Each disease-carrying haplotype is represented by a uniquely patterned bar. Inferred microsatellite typings are indicated by parentheses, and unknown alleles are indicated by "0". Loci in haplotypes ordered from top to bottom are REN158P08, REN128E21, REN107H05, CLN5, REN49C008, REN69E24, FH3411, REN89O04, and REN122L13. Individuals 78, 813, 52, and 823 share a common ancestor in a known NCL carrier several generations back. The ancestry of individual 823 can be traced back to another known carrier

Only a single nucleotide change at 619 bp of the CLN5 coding sequence (c.619C→T) in exon 4 (FIG. 2) was observed to cosegregate with the disease allele in Border collies in an autosomal recessive manner (FIG. 3). This transition results in replacement of the $Gln_{207}$ residue with a termination codon. An additional MseI restriction site is present in the disease allele that results in a fragment of 131 bp being cut into pieces of 64 and 67 bp (FIG. 2). No other sequence differences in CLN5 were observed between the Border collie and the poodle and boxer. The disease allele is relatively rare (approximately 3.5%) in the general Border collie population but found in all carriers tested (Table 3).

Of the 11 Australian pedigrees and 1 Japanese pedigree, only 1 did not contain the mutation within exon 4 (Table 3). This pedigree contained a single affected individual that was not closely related to any known carriers of NCL.

The canine CLN5 protein is predicted to be 350 amino acids in length, with high similarity to homologues in other species (FIG. 4). As reported elsewhere (Holmberg et al., 2004, supra), conservation is much lower within the 5' end of the first exon than within the remainder of the polypeptide. The beginning of the protein sequence is more similar to porcine than to human or mouse (FIG. 4) and also similar to bovine.

Materials and Methods

Sample Collection

Samples were collected from 96 Border collies from 11 Australian pedigrees, including 24 affected animals and 27 obligate carriers. Additional animals were also obtained for control purposes. One NCL-affected animal from Japan that was a descendent of Australian stock was also included. Diagnosis of the disease was made by observations of symptoms in conjunction with pathology demonstrating autofluorescence of accumulated lipopigment and positive staining with Sudan black, luxol-fast blue, and/or periodic acid Schiff.

DNA was extracted from blood using a salting-out protocol (Kunkel, et al., 1977, *Proc. Natl. Acad. Sci. USA* 74:1245-1249) and buccal cells using the Puregene DNA isolation kit (Gentra, Minneapolis, Minn., USA). A variation of published methods (Isola et al., 1994, *Am. J. Pathol.* 145:1301-1308) was used to extract DNA from a paraffin-embedded fixed brain tissue of one confirmed case of NCL. Tissues suitable for RNA extraction from affected animals proved too difficult to obtain.

Marker Selection

Loci were investigated as candidates of Border collie NCL, based on shared characteristics between the dog disease and other characterized forms of NCL. Four microsatellite markers (FH2561, COS6, AHT109, FH2576) were chosen from the region on canine chromosome 6 (CFA06) (Breen et al., 2001, supra; Mellersch et al., 2000, *Mamm. Genome* 11:120-130; Werner et al., 1999, *Mamm. Genome* 10:814-823) containing the identified canine homolog of CLN3 (Breen et al., 2001, supra). Fifteen additional microsatellite markers were selected on CFA37 that included markers linked to English setter NCL (Kirkness et al., 2003, supra; Lingaas et al., 1998, supra). Canine microsatellite markers (FIG. 1 and Table 5) from CFA22 (Breen et al., 2001, supra; Guyon et al., 2003, supra; Jouquand et al. 2000, *Anim Genet* 31:266-272) were selected from a region homologous to human 13q21.1-q32 containing CLN5 (Guyon et al., 2003, supra).

Microsatellite Typing and Linkage Analysis

Each 5 μl PCR was performed in an ABI 877 integrated thermal cycler. Reactions contained 25 ng of genomic DNA, 50 mM KCl, 10 mM Tris-HCl (pH 8.3), 0.5 μM each oligonucleotide primer, 200 AM each dNTP, 2.5 mM MgC12, and 0.5 U AmpliTaq Gold polymerase (Applied Biosystems, Foster City, Calif., USA). An initial denaturation step of 95° C. for 12 min was followed by 30 cycles of 95° C. for 15 s, 55° C. for 30 s, and 72° C. for 60 s with a final extension step of 72° C. for 10 min.

Microsatellite products were analyzed on ABI 377 or 3730 DNA sequencers and sized using Genescan and Genotyper software (Applied Biosystems). Multipoint linkage analysis was performed using GeneFlunter version 2.0 (Daly et al. 1998). Population allele frequencies were estimated from 96 unrelated individuals that did not have an identified NCL carrier ancestor within the previous three generations. Lod scores were calculated using an estimated disease allele frequency of 0.01 and recessive inheritance with complete penetrance.

CLN5 Candidate Gene Analysis

The canine CLN5 gene sequence was identified by searching whole genome sequences of two dog breeds. The amino acid sequence of human CLN5 (GenBank Accession No. AAC27614) was used to search the poodle (GenBank Accession No. AACN000000000) (Kirkness et al., 2003, supra) with TBLASTN (Table 6). The nucleotide sequences of the coding region of human CLN5 (GenBank Accession No. AF068227) was used to search the boxer genome (GenBank Accession No. AAEX00000000) with BLASTN (Table 6). Primer sites (Table 4) were designed from contigs identified from the poodle genome to amplify exons of dog CLN5. Primers were designed to putative introns using FASTPCR or PRIMER3. PCR was performed in 10 μl reactions with similar conditions for microsatellite amplification, except with cycles of 95° C. for 30 s, 56 or 59° C. (Table 4) for 60 s, and 72° C. for 60 s. A final extension at 72° C. for 5 min was used to complete the reaction.

PCR products were purified using AcroPrep 100K 96-well filter plates (PALL, Ann Arbor, Mich., USA) and sequencing was conducted using forward primers with BigDye Terminator version 3.1 chemistry (Applied Biosystems). Unaffected animals not closely related to NCL cases were also typed for the disease allele. Alignment of human CLN5 protein (AAC27614) with predicted amino acid sequences of mouse (XP_127882), pig (translated consensus of CJ022427 and BI182240), and dog was created with ClustalX 1.83 (Thompson et al., 1997, *Nucleic Acids Res.* 25:4876-4882) and displayed using the BoxShade 3.21 program.

TABLE 3

Genotype at CLN5 of the putative NCL disease allele in clinically diagnosed affected animals, their parents, or offspring (obligate carriers) and control samples obtained from animals without a known carrier in the preceding three generations

| | Number of each genotype | | |
|---|---|---|---|
| Disease status | T/T | C/T | C/C |
| Affected (n = 7) | 6 | 0 | 1 |
| Obligatory carriers (n = 16) | 0 | 16 | 0 |
| Controls (n = 86) | 0 | 3 | 83 |

TABLE 4

Primers used to sequence canine CLN5 exons and detect RFLP associated with NCL

| Exon | Forward primer | Reverse primer | Annealing temperature |
|---|---|---|---|
| 2 | TGATGACAGGCTGGATCTCACG (SEQ ID NO: 9) | TGTGCAAGAAGAACCAAACTCC (SEQ ID NO: 13) | 56° C. |
| 3 | ACAGGTGACACTTGGCATGAGC (SEQ ID NO: 10) | TCTGAGATAAGCAGCAATGGTC (SEQ ID NO: 14) | 56° C. |
| 4 | TTTGCTTTGGTGTTCACATAGG (SEQ ID NO: 11) | TTCTGCTCCAAGGCAGAAAG (SEQ ID NO: 15) | 59° C. |
| RFLP | TTTGCTTTGGTGTTCACATAGG (SEQ ID NO: 12) | CCCAAGTAGGTAGGTTCTCCA (SEQ ID NO: 16) | 59° C. |

TABLE 5

Location of microsatellite markers on radiation hybrid map (Guyon et al. 2003, supra) used to test for linkage of Border Collie NCL to the canine homologue of CLN5 on CFA22. Approximate locations in Mb are given from assembled dog genome V1.1.

| TSP units[a] | Approx Mb | Microsatellite Marker | Original Reference |
|---|---|---|---|
| 2369 | 22.197 | Ren158P08 | (Breen et al. 2001, supra) |
| 2498 | 24.607 | Ren128E21 | (Breen et al. 2001, supra) |
| 2646 | 26.411 | Ren107H05 | (Breen et al. 2001, supra) |
| 2717 | 30.658 | Ren49C08 | (Jouquand et al. 2000, supra) |
| 3025 | 32.933 | Ren69E24 | (Breen et al. 2001, supra) |
| 3263 | 39.683 | Ren89O04 | (Breen et al. 2001, supra) |
| 3286 | 39.679 | FH3411 | (Guyon et al. 2003, supra) |
| 3380 | 41.765 | Ren122L13 | (Breen et al. 2001, supra) |

[a]Map units defined by the TSP/CONCORDE program (Agarwala et al. 2000, Genome Res 10: 350-364)

TABLE 6

Sequence matches in canine genome to amino acid coding sequence of human CLN5.

| Exon[a] | Poodle[b] | Boxer (CFA22)[c] |
|---|---|---|
| 1 | No match | 335004604-335004752 |
| 2 | AACN010066999 2030-1865 bp | 335006444-335006609 |
| 3 | AACN010066999 957-732 bp | 335007517-335007742 |
| 4 | AACN010965587 637-126 bp | 335010542-335011053 |

[a]Untranslated regions not included.
[b]Genbank Accession Number with location of match to exon.
[c]Location in base pairs of match in assembled dog genome V1.1.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Adams (1983) *J. Am. Chem. Soc.* 105:661
Agarwala R, Applegate D L, Maglott D, Schuler G D, Schaffer A A (2000) A Fast and Scalable Radiation Hybrid Map Construction and Integration Strategy. *Genome Res* 10:350-364
Akimaru (1995) *Cylokines Mol. Ther.* 1:197-210
al-Obeidi (1998) *Mol. Biolechnol.* 9:205-223
Altschul et al. *Nucl. Acids Res.* 25: 3389, 1997
Altschul et al., *J. Mol. Biol.* 215(3):403-410, 1990
Altschul et al., *Nature Genetics* 3:266-272, 1993
Alving (1995) *Immunol. Rev.* 145:5-31
Ausubel et al. "Current Protocols in Molecular Biology" John Wiley & Sons Inc, Chapter 15, 1994-1998
Baguisi (1999) *Nat. Biotechnol.* 17:456-461
Bai (1997) *J. Neuroimmunol.* 80:65-75
Baltimore, *J. Virol.* 54: 401-407, 1985
Bandyopadhyay and Temin, *Mol. Cell. Biol.* 4: 749-754, 1984
Banga, A. K., Therapeutic Peptides and Proteins, Formulation, Processing and Delivery Systems (1995) Technomic Publishing Co., Lancaster, Pa.
Barringer (1990) *Gene* 89:117
Beaucage (1981) *Tetra. Lett.* 22:1859
Belousov (1997) *Nucleic Acids Res.* 25:3440-3444
Berger (1987) *Methods Enzymol.* 152:307-316
Berglund et al., *Biotechnology* 11: 916-920, 1993
Berkner et al., *BioTechniques* 6; 616-629, 1988
Berkner, *Curr. Top. Microbiol. Immunol.* 158: 39-66, 1992
Blommers (1994) *Biochemistry* 33:7886-7896
Bonner and Laskey, *Eur. J. Biochem.* 46: 83, 1974
Bowtell (1999) *Nature Genetics Supp.* 21:25-32
Breakefield and Geller, *Mol. Neurobiol.* 1: 339-371, 1987
Breen M, Jouquand S, Renier C, Mellersh C S, Hitte C, Holmes N G, Cheron A, Suter N, Vignaux F, Bristow A E, Priat C, McCann E, Andre C, Boundy S, Gitsham P, Thomas R, Bridge W L, Spriggs H F, Ryder E J, Curson A, Sampson J, Ostrander E A, Binns M M, Galibert F (2001) Chromosome-specific single-locus FISH probes allow anchorage of an 1800-marker integrated radiation-hybrid/linkage map of the domestic dog genome to all chromosomes. *Genome Res* 11: 1784-1795
Brenner and Lerner., (1992)
Bronson R T, Donahue L R, Johnson K R, Tanner A, Lane P W, Faust J R (1998) Neuronal ceroid lipofuscinosis (nclf), a new disorder of the mouse linked to Chromosome 9. *Am J Med Genet* 77:289-297
Bronson R T, Lake B D, Cook S, Taylor S, Davisson M T (1993) Motor-Neuron Degeneration of Mice Is a Model of Neuronal Ceroid Lipofuscinosis (Battens Disease). *Ann Neurol* 33:381-385
Broom M F, Zhou C M, Hill D F (1999) Progress toward positional cloning of ovine neuronal ceroid lipofuscinosis, a model of the human late-infantile variant CLN6. *Molecular Genetics and Metabolism* 66:373-375
Brown (1979) *Meth. Enzymol.* 68:109
Buchschacher and Panganiban, *J. Virol.* 66: 2731-2739, 1992
Burg (1996) *Mol. Cell. Probes* 10:257-271
Campbell (1994) *J. Org. Chem.* 59: 658
Capon (1989) *Nature* 377:525-531 (1989)
Caruthers (1980) *Nucleic Acids Res. Symp. Ser.* 215-223
Chen (1994) *J. Amer. Chem. Soc.* 116: 2661
Cho (1993) *Science* 261:1303
Christian R. B et al., (1992)
Cole (1985) in Monoclonal Antibodies and Cancer Therapy, Alan R. Liss, Inc., pp. 77-96
Colliuod (1993) *Bioconjugate Chem.* 4:528-536
Daly et al. 1998, GENEHUNTER 2.0—a complete linkage analysis system, *Am. J. Hum. Genet. Suppl.* 63, A286
Devlin et al., (1990)
Dobeli (1998) *Protein Expr. Purif* 12:404-14
Egleton (1997) "Bioavailability and transport of peptides and peptide drugs into the brain" *Peptides* 18:1431-1439
Eichler et al., *Med. Res. Rev.* 15:481-496 (1995)
Erb et al., (1994)
Fink et al., *Ann. Rev. Neurosci.* 19: 265-287, 1996
Fink et al., *Hum. Gene Ther.* 3: 11-19, 1992
Fix (1996) *Pharm Res.* 13:1760-1764
Fodor S P, Read J L, Pirrung M C, Stryer L, Lu A T, Solas D. (1991) *Science* 251(4995):767
Francis et al., *Curr. Opin. Chem. Biol.,* 2:422-428 (1998)
Freese et al., *Biochem. Pharmacol.* 40: 2189-2199, 1990
Frenkel (1995) *Free Radic. Biol. Med.* 19:373-380
Furka (1991) *Int. J. Pept. Prot. Res.,* 37: 487-493
Gallop et al. (1994) 37(9): 1233-1250
Gonnet et al., *Science* 256:1443-1445, 1992
Gordon et al., *Acc. Chem. Res.* 29:144-154 (1996)
Gordon et al., *J. Med. Chem.* 37:1233-1251 (1994)
Gordon et al., *J. Med. Chem.* 37:1385-1401 (1994)

Gorziglia and Kapikian, *J. Virol.* 66: 4407-4412, 1992

Guatelli (1990) *Proc. Natl. Acad. Sci. USA* 87:1874

Gupta P, Soyombo A A, Atashband A, Wisniewski K E, Shelton J M, Richardson J A, Hammer R E, Hofmann S L (2001) Disruption of PPT1 or PPT2 causes neuronal ceroid lipofuscinosis in knockout mice. *Proc Natl Acad Sci USA* 98:13566-13571

Gurun (1997) *Anesth Analg.* 85:317-323

Guyon R, Lorentzen T D, Hitte C, Kim L, Cadieu E, Parker H G, Quignon P, Lowe J K, Renier C, Gelfenbeyn B, Vignaux F, DeFrance H B, Gloux S, Mahairas G G, Andre C, Galibert F, Ostrander E A (2003) A 1-Mb resolution radiation hybrid map of the canine genome. *Proc Natl Acad Sci USA* 100:5296-5301

Hagihara (1992) *J. Amer. Chem. Soc.* 114: 6568

Harlow (1988) Antibodies, A Laboratory Manual, Cold Spring Harbor Publications, New York Harper P A, Walker K H, Healy P J, Hartley W J, Gibson A J, Smith J S (1988) Neurovisceral ceroid-lipofuscinosis in blind Devon cattle. *Acta Neuropathol* 75:632-636

Helseth et al., *J. Virol.* 64: 2416-2420, 1990

Henikoff & Henikoff (1989) *Proc. Natl. Acad. Sci. USA* 89:10915

Henikoff and Henikoff, *Proteins* 17:49-61, 1993

Higgins et al., *Methods Enzymol.* 266:383-402, 1996

Hirschmann (1992) *J. Amer. Chem. Soc.* 114: 9217-9218

Hobbs (1993) *Proc. Nat. Acad. Sci. USA* 90: 6909-6913

Holmberg V, Jalanko A, Isosomppi J, Fabritius A L, Peltonen L, Kopra O (2004) The mouse ortholog of the neuronal ceroid lipofuscinosis CLN5 gene encodes a soluble lysosomal glycoprotein expressed in the developing brain. *Neurobiology of Disease* 16:29

Holmberg V, Lauronen L, Autti T, Santavuori P, Savukoski M, Uvebrant F, Hofman 1, Peltonen L, Jarvela 1 (2000) Phenotype-genotype correlation in eight patients with Finnish variant late infantile NCL (CLN5). *Neurology* 55:579-581

Hoogenboom (1997) *Trends Biotechnol.* 15:62-70

Horn (1980) *Nucleic Acids Res. Symp. Ser.* 225-232

Houghten et al., (1992)

Houghton et al. (1991) *Nature,* 354: 84-88

Houweling P. Tammen I, Cavanagh J A L, Palmer D N, Raddsma H W (2004) Genetic characterisation of two animal models for Neuronal Ceroid Lipofuscinoses (NCL): the Australian Merino sheep and Devon cattle. Paper presented at International Society of Animal Genetics. Tokyo, Japan Hruby (1997) *Curr. Opin. Chem. Biol.* 1:114-119

Isola et al., 1994, Analysis of changes in DNA sequence copy number by comparative genomic hybridization in archival paraffin-embedded tumor samples, *Am. J. Pathol.* 145: 1301-1308

Isosomppi J, Vesa J, Jalanko A, Peltonen L (2002) Lysosomal localization of the neuronal ceroid lipofuscinosis CLN5 protein. *Hum Mol Genet* 11:885-891

Iwane (1997) *Biophys. Biochem. Res. Comm.* 230:76-80

Jayawickreme et al., (1994)

Johann (1992) *J. Virol.* 66:1635-1640

Johnson et al., *J. Virol.* 66: 2952-2965, 1992

Johnston (1998) *Curr. Biol.* 8:R171-R174

Jolly R D (1977) Neuronal Ceroid-Lipofuscinosis-Ovine Model. *N Z Med J* 86:304-304

Jolly R D, Palmer D N, Studdert V P, Sutton R H, Kelly W R, Koppang N, Dahme G, Hartley W J, Patterson J S, Riis R C (1994) Canine Ceroid Lipofuscinoses: A review and classification. *J Small Anim Pract* 35:299-306

Jouquand S, Priat C, Hitte C, Lachaume P, Andre C, Galibert F (2000) Identification and characterization of a set of 100 tri- and dinucleotide microsatellites in the canine genome. *Anim Genet* 31:266-272

Karlin & Altschul (1993) *Proc. Natl. Acad. Sci. USA* 90:5873

Katz (1997) *Annu. Rev. Biophys. Biomol. Struct.* 26:27-45

Kay et al., (1993)

Kazal et al., 1996

Kern (1997) *Biotechniques* 23:120-124

Kirkness E F, Bafna V, Halpern A L, Levy S. Remington K, Rusch D B, Delcher A L, Pop M, Wang W, Fraser C M, Venter J (2003) The Dog Genome: Survey Sequencing and Comparative Analysis. *Science* 301:1898-1903

Kohler and Milstein, *Nature* 256: 495-499, 1975 Koike M, Nakanishi H, Saftig P, Ezaki J, Isahara K, Ohsawa Y, Schulz-Schaeffer W, Watanabe T, Waguri S, Kametaka S, Shibata M, Yamamoto K, Kominami E, Peters C, von Figura K, Uchiyama Y (2000) Cathepsin D deficiency induces lysosomal storage with ceroid lipofuscin in mouse CNS neurons. *J Neurosci* 20:6898-6906

Koppang N (1973) Canine ceroid-lipofuscinosis—A model for human neuronal ceroid-lipofuscinosis and aging. *Mechanisms of Ageing and Development* 2:421-445

Kopra O, Vesa J, von Schantz C, Manninen T, Minye H, Fabritius A L, Rapola J, Diggelen O P, Saarela J, Jalanko A, Peltonen L (2004) A mouse model for Finnish variant late infantile neuronal ceroid lipofuscinosis, CLN5, reveals neuropathology associated with early aging. *Hum Mol Genet* 13:2893-2906

Kroll (1993) *DNA Cell. Biol.,* 12:441-53

Kuhn, *Science* 269: 1427-9 (1995)

Kunkel, et al., 1977, Analysis of human Y-chromosome-specific reiterated DNA in chromosome variants, *Proc. Natl. Acad. Sci. USA* 74:1245-1249

Kwoh (1989) *Proc. Natl. Acad. Sci. USA* 86:1173

Lam et al., (1991)

Landegren (1988) *Science* 241:1077

Langer (1990) *Science* 249:1527-1533

Lenstra., (1992)

Liang et al. (1996) *Science* 274: 1520-1522

Lindblad-toh K, Birren B, Nusbaum C, Abebe A, Abouelleil A, Adekoya E, Ait-zahra M, et al. (2004) The genome sequence of *Canis familiaris*. Vol. 2004, pp *Canis familiaris* chromosome 22 cont__10622, whole genome shotgun sequence Lingaas F, Aarskaug T. Sletten M. Bjerkas I, Grimholt U, Moe L, Juneja R K, Wilton A N, Galibert F, Holmes N G, Dolf G (1998) Genetic markers linked to neuronal ceroid lipofuscinosis in English setter dogs. *Anim Genet* 29:371-376

Lu (1995) *Anal. Chem.* 67:83-87

Madzak et al., *J. Gen. Virol.* 73: 1533-1536, 1992

Margolskee, *Curr. Top., Microbiol. Immunol.* 158: 67-95, 1992

Mata (1997) *Toxicol. Appl. Pharmacol.* 144:189-197

Mattheakis et al., (1994)

Medynski., (1994)

Mellersch et al., 2000, An integrated linkage-radiation hybrid map of the canine genome, *Mamm. Genome* 11:120-130

Merrifield (1997) *Methods Enzymol.* 289:3-13

Miller et al., *J. Virol.* 62: 4337-4345, 1988

Miller et al., *Mol. Cell. Biol.* 5: 431-437, 1985

Miller, *Curr. Top. Microbiol. Immunol.* 158: 1-24, 1992

Mitchison H M, Bernard D J, Greene N D E, Cooper J D, Junaid M A, Pullarkat R K, de Vos N, Breuning M H, Owens J W, Mobley W C, Gardiner R M, Lake B D, Taschner P E M, Nussbaum R L (1999) Targeted disruption of the Cln3 gene provides a mouse model for Batten disease. Neurobiology of Disease 6:321-334

Mole S E (1999) Batten's disease: eight genes and still counting? *Lancet* 354:443-445

Moore, A., Basilion, J., Chiocca, E., and Weissleder, R., *BBA,* 1402.239-249, 1988

Moss, *Curr. Top. Microbiol. Immunol.* 158: 25-38, 1992

Moss, *Proc. Nail. Acad. Sci. USA* 93: 11341-11348, 1996

Muzyczka, *Curr. Top. Microbiol. Immunol.* 158: 97-129, 1992

Nakao et al., *Exp. Anim.* 47:167-71 (1998)

Naldini et al., *Science* 272: 263-267, 1996

Narang (1979) *Meth. Enzymol.* 68:90

Ng (1995) *Langmuir* 11:4048-55

Ohi et al., *Gene* 89: 279-282, 1990

Ohlmeyer et al., (1993)

Okada (1996) *Gene Ther.* 3:957-964

Ostergaard (1997) *Mol. Divers.* 3:17-27

Ostresh (1996) *Methods Enzymol.* 267:220-234

Page et al., *J. Virol.* 64: 5270-5276, 1990

Patton (1998) *Biotechniques* 16:141-143

Pearson and Lipman, *Proc. Natl. Acad. Sci. USA* 85(8):2444-2448, 1988

Petropoulos et al., *J Viol.* 66: 3391-3397, 1992

Pollock (1999) *J. Immunol. Methods* 231:147-157

Quantin et al., *Proc. Natl. Acad. Sci. USA* 89: 2581-2584, 1992

Ranta S, Zhang Y, Lonka L, Messer A, Mole S, Wheeler R, Sharp J, Hirvasniemi A, de la Chapelle A, Gilliam T C, Lehesjoki A E (1999) Neuronal ceroid lipofuscinosis: A novel gene (CLN8) is mutated in human progressive epilepsy with mental retardation and the motor neuron degeneration mouse model. *Am J Hum Genet* 65:A5-A5

Rideout et al., *Cell* 109: 17-27 (2002)

Rideout et al., *Nat. Genet.* 24: 109-10 (2000)

Roberge (1995) *Science* 269:202

Roberts (1987) *Nature* 328:731

Rosenfeld et al., *Cell* 68: 143-155, 1992

Russell and Hirata, *Nature Genetics* 18: 323-328, 1998

Salmon et al., (1993)

Samanen (1996) *J. Pharm. Pharmacol.* 48:119-135

Samstag (1996) *Antisense Nucleic Acid Drug Dev* 6:153-156

Santavuori P R, Rapola J, Haltia M, Tyynela J, Peltonen L, Mole S E (1999) CLN5. Finnish Variant Late Infantile NCL. In: Goebel H H, Mole S E, Lake B D (eds) The Neuronal Ceroid Lipofuscinoses (Batten disease). IOS Press, Oxford, pp 91-101

Santavuori P R, Rapola J, Sainio K, Raitta C (1982) A variant of Jansky-Bielschowsky disease. *Neuropediatrics* 13:135-141

Savukoski M, Klockars T, Holmberg V, Santavuori P, Lander E S, Peltonen L (1998) CLN5, a novel gene encoding a putative transmembrane protein mutated in Finnish variant late infantile neuronal ceroid lipofuscinosis. *Nature Genet* 19:286-288

Sayani (1996) "Systemic delivery of peptides and proteins across absorptive mucosae" *Crit. Rev. Ther. Drug Carrier Syst.* 13:85-184

Schneider (1995) *Protein Expr. Purif.* 6435:10

Schneider et al., *Nature Genetics* 18: 180-183, 1998

Schuhmann (1991) *Adv. Mater.* 3:388-391

Schummer (1997) *Biotechniques* 23:1087-1092

Schwartz and Dayhoff, eds., 1978, Matrices for Detecting Distance Relationships: Atlas of Protein Sequence and Structure, Washington: National Biomedical Research Foundation Scott and Smith., (1990)

Shimada el al., *J. Clin. Invest.* 88: 1043-1047, 1991

Sigal (1996) *Anal. Chem.* 68:490-497

Sleat D E, Wiseman J A, Lobel P (2003) A mouse model for classical late-infantile neuronal ceroid lipofuscinosis (LINCL). Paper presented at 9th International Congress on Neuronal Ceroid Lipofuscinoses. Chicago Smith (1997) *J. Clin. Microbiol.* 35:1477-1491

Sofia, Molecule. *Divers.,* 3:75-94 (1998)

Solinas-Toldo (1997) *Genes, Chromosomes & Cancer* 20:399-407

Sooknanan (1995) *Biotechnology* 13:563-564

Sorge et al., *Mol. Cell. Biol.* 4: 1730-1737, 1984

Spatola (1983) in *Chemistry and Biochemistry of Amino Acids, Peptides and Proteins*, Vol. 7, pp 267-357, "Peptide Backbone Modifications," Marcell Dekker, NY-ESO Stratford-Perricaudet et al., *Hum. Gene Ther.* 1: 241-256, 1990

Strauss-Soukup (1997) *Biochemistry* 36:8692-8698

Studdert V P, Mitten R W (1991) Clinical features of ceroid lipofuscinosis in border collie dogs. *Aust Vet J* 68:137-140

Summerton and Weller, *Antisense and Nucleic Acid Drug Development* 7: 187-195, 1997

Suntres (1994) *J. Pharm. Pharmacol.* 46:23-28

Szoka (1980) *Ann. Rev. Biophys. Bioeng.* 9:467

Taylor R, Farrow B (1988) Ceroid-lipofuscinosis in border collie dogs. *Acta Neuropathol* 75:627-631

Thompson et al., *Nucleic Acids Res.* 22(2):4673-4680, 1994

Thompson et al., 1997, The CLUSTAL_X Windows interface: flexible strategies for multiple sequence alignment aided by quality analysis tools, *Nucleic Acids Res.* 25:4876-4882

Tietze et al., *Curr. Biol.,* 2:363-381 (1998)

Tonegawa (1997) *J. Exp. Med.* 186:507-515

Tyynela J, Palmer D N, Baumann M, Haltia M (1993) Storage of saposins A and D in infantile neuronal ceroid-lipofuscinosis. FEBS Letters 330:8-12

Tyynela J, Sohar I, Sleat D E, Gin R M, Donnelly R J, Baumann M, Haltia M, Lobel P (2000) A mutation in the ovine cathepsin D gene causes a congenital lysosomal storage disease with profound neurodegeneration. *Embo J* 19:2786-2792

Url A, Bauder B, Thalhammer J, Nowotny N, Kolodziejek J, Herout N, Furst S. Weissenbock H (2001) Equine neuronal ceroid lipofuscinosis. *Acta Neuropathol* 101:410

Vaughn (1996) *Nature Biotechnology* 14:309-314

Vesa A, Chin M H, Oelgeschlager K, Isosomppi J, DellAngelica EC, Jalanko A, Peltonen L (2002) Neuronal ceroid lipoluscinoses are connected at molecular level: interaction of CLN5 protein with CLN2 and CLN3. *Mol Biol Cell* 13:2410-2420

Vutla (1996) *J. Pharm. Sci.* 85:5-8

Ward et al., (1989) *Nature* 341:544-546

Warren (1997) *J. Neurol. Sci.* 152:31-38

Wedemeyer, N., Potter, T., Wetzlich, S. and Gohde, W. *Clinical Chemistry* 48:9 1398-1405, 2002

Weissleder, R., Moore, A., Ph.D., Mahmood-Bhorade, U., Benveniste, H., Chiocca, E. A., Basilion, J. P. *Nature Medicine,* 6.351-355, 2000

Werner et al., 1999, Anchoring of canine linkage groups with chromosome-specific markers, *Mamm. Genome* 10:814-823

Wilkinson et al., *Nucleic Acids Res.* 20: 2233-2239, 1992

Williams (1995) *Biochemistry* 34:1787-1797

Wilson (1994) *J. Immunol. Methods* 175:267-273

Wilson and Czarnik, eds., *Combinatorial Chemistry: Synthesis and Application*, John Wiley & Sons, New York (1997)

Woodle (1992) *Pharm. Res.* 9:260-265

Woon (1998) *Genomics* 50:306-316

Wu (1989) *Genomics* 4:560

Yarmush (1992) *J. Biochem. Biophys. Methods* 25:85-97

Yoshikawa M, Uchida S, Ezaki J, Rai T, Hayama A, Kobayashi K, Kida Y, Noda M, Koike M, Uchiyama Y, Marumo F, Kominami E, Sasaki S (2002) CLC-3 deficiency leads to phenotypes similar to human neuronal ceroid lipofuscinosis. *Genes Cells* 7:597-605

Zalipsky (1995) *Bioconjug. Chem.* 6:705-708

---

The invention claimed is:

1. A method for screening a canine for neuronal ceroid lipofuscinosis or a predisposition to neuronal ceroid lipofuscinosis or being a carrier of neuronal ceroid lipofuscinosis comprising:
providing a biological sample from said canine; and
identifying the presence or absence of one or more mutations in the ceroid lipofuscinosis neuronal 5 (CLN5) gene or CLN5 protein, wherein said gene comprises exons 1-4 of SEQ ID NO: 1 and said protein comprises SEQ ID NO:2 and wherein at least one of said mutations is a C619T substitution of the CLN5 gene or a deletion of amino acid 207 residue of the CLN5 protein.

2. The method according to claim 1, wherein said amino acid is glutamine.

3. The method according to claim 2, wherein said mutation is the deletion of glutamine 207.

4. The method according to claim 3, wherein deletion corresponds to a Gln207Stop mutation.

5. The method according to claim 4, wherein said Gln207Stop mutation results in truncation of the CLN5 protein at residue 207.

6. The method according to claim 1, wherein said biological sample is a sample containing genomic DNA.

7. The method of claim 1, wherein said canine is a Border Collie.

8. A method of identifying the presence or absence of neuronal ceroid lipofuscinosis, or a predisposition to developing neuronal ceroid lipofuscinosis in a canine or identifying a canine which is a carrier of neuronal ceroid lipofuscinosis comprising:
providing a biological sample from a canine; and
identifying the presence or absence of a C619T substitution mutation in a CLN5 gene in said biological sample, wherein said gene comprises exons 1-4 of SEQ ID NO:1.

9. The method of claim 8, wherein said canine is a Border Collie.

10. A method of identifying the presence or absence of a variant CLN5 gene associated with storage neuronal ceroid lipofuscinosis disease in a canine comprising:
providing a biological sample from a canine; and
identifying the presence or absence of a C619T substitution mutation in a CLN5 gene in said biological sample, wherein said gene comprises exons 1-4 of SEQ ID NO:1.

11. The method of claim 10, wherein said canine is a Border Collie.

* * * * *

UNITED STATES PATENT AND TRADEMARK OFFICE
CERTIFICATE OF CORRECTION

PATENT NO. : 7,723,034 B2  
APPLICATION NO. : 11/351183  
DATED : May 25, 2010  
INVENTOR(S) : Scott Andrew Melville and Alan Norman Wilton Page 1 of 3

It is certified that error appears in the above-identified patent and that said Letters Patent is hereby corrected as shown below:

Title Page (Item 54) Title, Line 2, Change "LIPFUSCINOSIS" to --LIPOFUSCINOSIS--.

Title Page (Item 54) Title, Line 4, Change "NEUORNAL" to --NEURONAL--.

In Column 1, Line 2, Change "LIPFUSCINOSIS" to --LIPOFUSCINOSIS--.

In Column 1, Line 4, Change "NEUORNAL" to --NEURONAL--.

In Column 4, Line 2, Change "cytoseine" to --cytosine--.

In Column 4, Line 6, Change "Gin" to --Gln--.

In Column 5, Line 38, Change "Gin" to --Gln--.

In Column 7, Line 29, Change "96%" to --96%,--.

In Column 8, Line 18, Change "NCL," to --NCL--.

In Column 10, Line 9, After "carrier" insert --.--.

In Column 10, Line 53, Change "lipfuscinosis" to --lipofuscinosis--.

In Column 16, Line 12 (Table 2), Change "L-N-methylisolleucine" to --L-N-methylisoleucine--.

In Column 16, Line 32 (Table 2), Change "α-methylcylcopentylalanine" to --α-methylcyclopentylalanine--.

In Column 16, Line 33 (Table 2), Change "α-methyl-α-napthylalanine" to --α-menthyl-α-naphthylalanine--.

In Column 16, Line 39 (Table 2), Change "α-napthylalanine" to --α-naphthylalanine--.

In Column 16, Line 49 (Table 2), Change "N-cylcododecylglycine" to --N-cyclododecylglycine--.

In Column 16, Line 57 (Table 2), Change "N-(hydroxyethyl))glycine" to --N-(hydroxyethyl)glycine--.

Signed and Sealed this  
Twenty-eighth Day of December, 2010

David J. Kappos  
*Director of the United States Patent and Trademark Office*

CERTIFICATE OF CORRECTION (continued)

In Column 16, Line 58 (Table 2), Change "N-(imidazolylethyl))glycine" to --N-(imidazolylethyl)glycine--.

In Column 16, Line 59 (Table 2), Change "N-(3-indolylyethyl)glycine" to --N-(3-indolylethyl)glycine--.

In Column 16, Line 68, Change "N-methyla-napthylalanine" to --N-methyl-α-naphthylalanine--.

In Column 18, Line 41, Change "naphylalanine" to --naphthylalanine--.

In Column 18, Line 50 (Approx.), Change "L1-alkylalinines" to --L-alkylalanines--.

In Column 19, Line 39, Change "diethylprocarbonate" to --diethylpyrocarbonate--.

In Column 20, Line 14, Change "Biolechnol." to --Biotechnol--.

In Column 24, Line 63, Change "baculoviridiae" to --baculoviridae--.

In Column 24, Line 63, Change "parvoviridiae, picornoviridiae" to --parvoviridae, picornaviridae--.

In Column 24, Lines 63-64, Change "herpesveridiae" to --herpesviridae--.

In Column 24, Line 64, Change "poxyiridae" to --poxviridae--.

In Column 24, Line 64, Change "adenoviridiae" to --adenoviridae--.

In Column 24, Line 64, Change "picornnaviridiae" to --picornaviridae--.

In Column 25, Line 58, Change "or the" to --of the--.

In Column 35, Lines 34-35, Change "Dernhardt's" to --Denhardt's--.

In Column 39, Line 58, Change "el al." to --et al.--.

In Column 46, Line 47, After "products" insert --.--.

In Column 46, Line 50, Change "-above." to --above.--.

In Column 48, Line 15, Change "6," to --6;--.

In Column 52, Lines 4-8, Delete "Such methods include northern blots, polymerase chain reaction after reverse transcription of RNA (RT-PCR), and nuclease protection. Measurement of a response of a pathway component can be performed using large scale gene expression methods." And insert the same on Col. 52, Line 3, after "formats." As a continuation of the paragraph.

In Column 53, Line 22, Change "Rainin." to --Rainin,--.

In Column 53, Line 38, Change "Inc." to --Inc.,--.

In Column 54, Line 14, Change "strepavidin" to --streptavidin--.

In Column 54, Lines 45-46, Change "pyridyidithio)" to --pyridyldithio)--.

In Column 67, Line 8 (Approx), Change "NCL," to --NCL--.

In Column 67, Line 29, Change "MgC12," to --MgCl2,--.

In Column 67, Line 38, Change "GeneFlunter" to -- GeneHunter--.

In Column 69, Line 52 (Approx), Change "Cylokines" to --Cytokines--.

In Column 69, Line 53 (Approx), Change "Biolechnol." to --Biotechnol--.

In Column 70, Line 58, Change "767" to --767-73--.

In Column 71, Line 33 (Approx.), Change "16:29" to --16:29-40--.

In Column 71, Line 35 (Approx.), Change "Hofman 1," to --Hofman I,--.

In Column 71, Line 35 (Approx.), Change "Jarvela 1" to --Jarvela I--.

In Column 71, Line 42, Change "Houweling P." to --Houweling P,--.

In Column 72, Line 10, Change "Levy S." to --Levy S,--.

In Column 72, Line 46 (Approx.), Change "Aarskaug T." to --Aarskaug T,--.

In Column 72, Line 46 (Approx.), Change "Sletten M." to --Sletten M,--.

In Column 73, Line 6, Change "1402.239-249," to --1402:239-249,--.

In Column 73, Line 8, Change "Nail." to --Natl.--.

In Column 73, Line 67, Change "el al.," to --et al.,--.

In Column 74, Line 42, Change "Furst S." to --Furst S,--.

In Column 74, Line 43, Change "101:410" to --101:410-414--.

In Column 74, Line 47, Change "lipoluscinoses" to --lipofuscinoses--.

In Column 74, Line 57, Change "6.351-355," to --6:351-355,--.

In Column 74, Line 58, Change "ofcanine" to --of canine--.

In Column 94, Line 57 (Approx.), In Claim 10, after "with" delete "storage".

SEQUENCE LISTING

```
<160> NUMBER OF SEQ ID NOS: 20

<210> SEQ ID NO 1
<211> LENGTH: 1053
<212> TYPE: DNA
<213> ORGANISM: Canis familiaris

<400> SEQUENCE: 1
atggcgcagg cggggagcgc cgaccccggg gtcggggggcc attgggccgc ggggcctcgg      60
tgcgcgcctt ggcgctgggc cctggcgctg ctgtggctgg cgacggccgc gggcggcccc     120
tcccggcgcc agtggcccgt gccctacaag cgcttttcct tccgtccaga accagatcct     180
tattgtcaag ctaaatacac attctgtcca actggctcac ctatcccagt tatgaaaggt     240
gatgatgtca ttgaagtctt ccggttacaa accccagtat gggaatttaa atatgggaac     300
ctcctgggac acttgaaaat tatgcatgat gccattggat tcaagagtac tttaactggc     360
aagaactaca caatggaatg gtatgaactt ttccaacttg gaaactgtac atttccccat     420
ctccgacctg aaatgaatgc ccctttctgg tgcaatcaag gcgctgcctg ttttttttgaa     480 gggattgatg atatccactg gaaggaaaat gggacgttag tactggtagc aaccatatca     540
ggaaacacat taaccaaat ggcaaagtgg gtaaagcggg acaatgaaac aggaatttat     600
tacgagacgt ggactgttca agccagccca acaaggggg ctgagacatg gtttgaatcc     660
tatgattgtt ctaaattcgt gttaaggaca tacaagaagt tggctgaact tggagcagag     720
ttcaagaaga tagaaaccaa ctatacaaga atatttcttt acagtggaga acctacctac     780
ttgggaaatg aaacctctat ttttgggccg acaggaaata agactcttgc tttagccata     840
aaaagatttt attacccctt caaaccacat ttatcaacta agaatttct gctcagtatc     900 ttgcaaattt tgatgcagt gattatacac agagagttt atttgtttta taatttgaa     960 tattggtttt tacctatgaa atttccttt attaaaataa catatgaaga aatcccttta    1020
cctaaaagaa atgaaacact ttctggtcta taa                                 1053

<210> SEQ ID NO 2
<211> LENGTH: 350
<212> TYPE: PRT
<213> ORGANISM: Canis familiaris

<400> SEQUENCE: 2

Met Ala Gln Ala Gly Ser Ala Asp Pro Gly Val Gly Gly His Trp Ala
  1               5                  10                  15

Ala Gly Pro Arg Cys Ala Pro Trp Arg Trp Ala Leu Ala Leu Leu Trp
             20                  25                  30

Leu Ala Thr Ala Ala Gly Gly Pro Ser Arg Arg Gln Trp Pro Val Pro
         35                  40                  45

Tyr Lys Arg Phe Ser Phe Arg Pro Glu Pro Asp Pro Tyr Cys Gln Ala
     50                  55                  60

Lys Tyr Thr Phe Cys Pro Thr Gly Ser Pro Ile Pro Val Met Lys Gly
 65                  70                  75                  80

Asp Asp Val Ile Glu Val Phe Arg Leu Gln Thr Pro Val Trp Glu Phe
                 85                  90                  95
```

```
Lys Tyr Gly Asn Leu Leu Gly His Leu Lys Ile Met His Asp Ala Ile
                100                 105                 110
Gly Phe Lys Ser Thr Leu Thr Gly Lys Asn Tyr Thr Met Glu Trp Tyr
            115                 120                 125
Glu Leu Phe Gln Leu Gly Asn Cys Thr Phe Pro His Leu Arg Pro Glu
        130                 135                 140
Met Asn Ala Pro Phe Trp Cys Asn Gln Gly Ala Ala Cys Phe Phe Glu
145                 150                 155                 160
Gly Ile Asp Asp Ile His Trp Lys Glu Asn Gly Thr Leu Val Leu Val
                165                 170                 175
Ala Thr Ile Ser Gly Asn Thr Phe Asn Gln Met Ala Lys Trp Val Lys
            180                 185                 190
Arg Asp Asn Glu Thr Gly Ile Tyr Tyr Glu Thr Trp Thr Val Gln Ala
        195                 200                 205
Ser Pro Thr Lys Gly Ala Glu Thr Trp Phe Glu Ser Tyr Asp Cys Ser
    210                 215                 220
Lys Phe Val Leu Arg Thr Tyr Lys Lys Leu Ala Glu Leu Gly Ala Glu
225                 230                 235                 240
Phe Lys Lys Ile Glu Thr Asn Tyr Thr Arg Ile Phe Leu Tyr Ser Gly
                245                 250                 255
Glu Pro Thr Tyr Leu Gly Asn Glu Thr Ser Ile Phe Gly Pro Thr Gly
            260                 265                 270
Asn Lys Thr Leu Ala Leu Ala Ile Lys Arg Phe Tyr Tyr Pro Phe Lys
        275                 280                 285
Pro His Leu Ser Thr Lys Glu Phe Leu Leu Ser Ile Leu Gln Ile Phe
    290                 295                 300
Asp Ala Val Ile Ile His Arg Glu Phe Tyr Leu Phe Tyr Asn Phe Glu
305                 310                 315                 320
Tyr Trp Phe Leu Pro Met Lys Phe Pro Phe Ile Lys Ile Thr Tyr Glu
                325                 330                 335
Glu Ile Pro Leu Pro Lys Arg Asn Glu Thr Leu Ser Gly Leu
            340                 345                 350

<210> SEQ ID NO 3
<211> LENGTH: 666
<212> TYPE: DNA
<213> ORGANISM: Canis familiaris

<400> SEQUENCE: 3
tttgctttgg tgttcacata ggtaattttt ttttttttta acctaggaaa cacatttaac     60
caaatggcaa agtgggtaaa gcgggacaat gaaacaggaa tttattacga cgtggact    120 gttcaagcca gcccaacaaa gggggctgag acatggtttg aatcctatga ttgttctaaa   180
ttcgtgttaa ggacatacaa gaagttggct gaacttggag cagagttcaa gaagatagaa   240
accaactata caagaatatt tctttacagt ggagaaccta cctacttggg aaatgaaacc   300 tctattttttg ggccgacagg aaataagact cttgctttag ccataaaaag atttattac    360 cccttcaaac cacatttatc aactaaagaa tttctgctca gtatcttgca aatttttgat   420
gcagtgatta tacacagaga gttttatttg ttttataatt ttgaatattg gttttttacct   480 atgaaattttc cttttattaa aataacatat gaagaaatcc ctttacctaa agaaatgaa    540 acactttctg gtctataaca tttttaattcc attgctcttt ttttccttct gtcaccagca   600
tatatatttt tcagggggtg attttacatt tgtggatttc ttaggccttt ctgccttgga    660
gcagaa                                                               666
```

<210> SEQ ID NO 4
<211> LENGTH: 170
<212> TYPE: PRT
<213> ORGANISM: Canis familiaris

<400> SEQUENCE: 4

Gly Asn Thr Phe Asn Gln Met Ala Lys Trp Val Lys Arg Asp Asn Glu
1               5                   10                  15

Thr Gly Ile Tyr Tyr Glu Thr Trp Thr Val Gln Ala Ser Pro Thr Lys
            20                  25                  30

Gly Ala Glu Thr Trp Phe Glu Ser Tyr Asp Cys Ser Lys Phe Val Leu
        35                  40                  45

Arg Thr Tyr Lys Lys Leu Ala Glu Leu Gly Ala Glu Phe Lys Lys Ile
    50                  55                  60

Glu Thr Asn Tyr Thr Arg Ile Phe Leu Tyr Ser Gly Glu Pro Thr Tyr
65                  70                  75                  80

Leu Gly Asn Glu Thr Ser Ile Phe Gly Pro Thr Gly Asn Lys Thr Leu
                85                  90                  95

Ala Leu Ala Ile Lys Arg Phe Tyr Tyr Pro Phe Lys Pro His Leu Ser
            100                 105                 110

Thr Lys Glu Phe Leu Leu Ser Ile Leu Gln Ile Phe Asp Ala Val Ile
        115                 120                 125

Ile His Arg Glu Phe Tyr Leu Phe Tyr Asn Phe Glu Tyr Trp Phe Leu
    130                 135                 140

Pro Met Lys Phe Pro Phe Ile Lys Ile Thr Tyr Glu Glu Ile Pro Leu
145                 150                 155                 160

Pro Lys Arg Asn Glu Thr Leu Ser Gly Leu
                165                 170

<210> SEQ ID NO 5
<211> LENGTH: 407
<212> TYPE: PRT
<213> ORGANISM: Homo sapiens

<400> SEQUENCE: 5

Met Arg Arg Asn Leu Arg Leu Gly Pro Ser Ser Gly Ala Asp Ala Gln
1               5                   10                  15

Gly Gln Gly Ala Pro Arg Pro Gly Leu Ala Ala Pro Arg Met Leu Leu
            20                  25                  30

Pro Pro Ala Ser Gln Ala Ser Arg Gly Ser Gly Ser Thr Gly Cys Ser
        35                  40                  45

Leu Met Ala Gln Glu Val Asp Thr Ala Gln Gly Ala Glu Met Arg Arg
    50                  55                  60

Gly Ala Gly Ala Ala Arg Gly Arg Ala Ser Trp Cys Trp Ala Leu Ala
65                  70                  75                  80

Leu Leu Trp Leu Ala Val Val Pro Gly Trp Ser Arg Val Ser Gly Ile
                85                  90                  95

Pro Ser Arg Arg His Trp Pro Val Pro Tyr Lys Arg Phe Asp Phe Arg
            100                 105                 110

Pro Lys Pro Asp Pro Tyr Cys Gln Ala Lys Tyr Thr Phe Cys Pro Thr
        115                 120                 125

Gly Ser Pro Ile Pro Val Met Glu Gly Asp Asp Ile Glu Val Phe
    130                 135                 140

Arg Leu Gln Ala Pro Val Trp Glu Phe Lys Tyr Gly Asp Leu Leu Gly
145                 150                 155                 160

-continued

```
His Leu Lys Ile Met His Asp Ala Ile Gly Phe Arg Ser Thr Leu Thr
            165                 170                 175
Gly Lys Asn Tyr Thr Met Glu Trp Tyr Glu Leu Phe Gln Leu Gly Asn
            180                 185                 190
Cys Thr Phe Pro His Leu Arg Pro Glu Met Asp Ala Pro Phe Trp Cys
            195                 200                 205
Asn Gln Gly Ala Ala Cys Phe Phe Glu Gly Ile Asp Asp Val His Trp
            210                 215                 220
Lys Glu Asn Gly Thr Leu Val Gln Val Ala Thr Ile Ser Gly Asn Met
225                 230                 235                 240
Phe Asn Gln Met Ala Lys Trp Val Lys Gln Asp Asn Glu Thr Gly Ile
            245                 250                 255
Tyr Tyr Glu Thr Trp Asn Val Lys Ala Ser Pro Glu Lys Gly Ala Glu
            260                 265                 270
Thr Trp Phe Asp Ser Tyr Asp Cys Ser Lys Phe Val Leu Arg Thr Phe
            275                 280                 285
Asn Lys Leu Ala Glu Phe Gly Ala Glu Phe Lys Asn Ile Glu Thr Asn
            290                 295                 300
Tyr Thr Arg Ile Phe Leu Tyr Ser Gly Glu Pro Thr Tyr Leu Gly Asn
305                 310                 315                 320
Glu Thr Ser Val Phe Gly Pro Thr Gly Asn Lys Thr Leu Gly Leu Ala
            325                 330                 335
Ile Lys Arg Phe Tyr Pro Phe Lys Pro His Leu Pro Thr Lys Glu
            340                 345                 350
Phe Leu Leu Ser Leu Leu Gln Ile Phe Asp Ala Val Ile Val His Lys
            355                 360                 365
Gln Phe Tyr Leu Phe Tyr Asn Phe Glu Tyr Trp Phe Leu Pro Met Lys
            370                 375                 380
Phe Pro Phe Ile Lys Ile Thr Tyr Glu Glu Ile Pro Leu Pro Ile Arg
385                 390                 395                 400
Asn Lys Thr Leu Ser Gly Leu
            405

<210> SEQ ID NO 6
<211> LENGTH: 341
<212> TYPE: PRT
<213> ORGANISM: Mus musculus

<400> SEQUENCE: 6

Met Leu Arg Gly Gly Pro Cys Gly Ala His Trp Arg Pro Ala Leu Ala
  1               5                  10                  15
Leu Ala Leu Leu Gly Leu Ala Thr Ile Leu Gly Ala Ser Pro Thr Ser
             20                  25                  30
Gly Gln Arg Trp Pro Val Pro Tyr Lys Arg Phe Ser Phe Arg Pro Lys
             35                  40                  45
Thr Asp Pro Tyr Cys Gln Ala Lys Tyr Thr Phe Cys Pro Thr Gly Ser
         50                  55                  60
Pro Ile Pro Val Met Lys Asp Asn Asp Val Ile Glu Val Leu Arg Leu
 65                  70                  75                  80
Gln Ala Pro Ile Trp Glu Phe Lys Tyr Gly Asp Leu Leu Gly His Phe
             85                  90                  95
Lys Leu Met His Asp Ala Val Gly Phe Arg Ser Thr Leu Thr Gly Lys
            100                 105                 110
Asn Tyr Thr Ile Glu Trp Tyr Glu Leu Phe Gln Leu Gly Asn Cys Thr
        115                 120                 125
```

```
Phe Pro His Leu Arg Pro Asp Lys Ser Ala Pro Phe Trp Cys Asn Gln
    130                 135                 140

Gly Ala Ala Cys Phe Phe Glu Gly Ile Asp Asp Lys His Trp Lys Glu
145                 150                 155                 160

Asn Gly Thr Leu Ser Val Val Ala Thr Ile Ser Gly Asn Thr Phe Asn
                165                 170                 175

Lys Val Ala Glu Trp Val Lys Gln Asp Asn Glu Thr Gly Ile Tyr Tyr
                180                 185                 190

Glu Thr Trp Thr Val Arg Ala Gly Pro Gly Gln Gly Ala Gln Thr Trp
                195                 200                 205

Phe Glu Ser Tyr Asp Cys Ser Asn Phe Val Leu Arg Thr Tyr Lys Lys
    210                 215                 220

Leu Ala Glu Phe Gly Thr Glu Phe Lys Lys Ile Glu Thr Asn Tyr Thr
225                 230                 235                 240

Lys Ile Phe Leu Tyr Ser Gly Glu Pro Ile Tyr Leu Gly Asn Glu Thr
                245                 250                 255

Ser Ile Phe Gly Pro Lys Gly Asn Lys Thr Leu Ala Leu Ala Ile Lys
                260                 265                 270

Lys Phe Tyr Gly Pro Phe Arg Pro Tyr Leu Ser Thr Lys Asp Phe Leu
    275                 280                 285

Met Asn Phe Leu Lys Ile Phe Asp Thr Val Ile Ile His Arg Gln Phe
    290                 295                 300

Tyr Leu Phe Tyr Asn Phe Glu Tyr Trp Phe Leu Pro Met Lys Pro Pro
305                 310                 315                 320

Phe Val Lys Ile Thr Tyr Glu Leu Thr Pro Leu Pro Thr Arg His Thr
                325                 330                 335

Thr Phe Thr Asp Leu
            340

<210> SEQ ID NO 7
<211> LENGTH: 356
<212> TYPE: PRT
<213> ORGANISM: Sus scrofa

<400> SEQUENCE: 7

Met Val Pro Ala Thr Ser Thr Gly Pro Gly Ala Gly Val Arg Arg Cys
1               5                   10                  15

Ala Gly Val Ala Leu Gly Arg Ala Pro Trp Ser Trp Gly Thr Ala Leu
                20                  25                  30

Leu Trp Leu Val Ala Ala Val Ala Ala Thr Ala Gly Ser Arg Ser Leu
            35                  40                  45

Arg Arg Trp Pro Val Pro Tyr Lys Arg Phe Ser Phe Arg Pro Glu Pro
    50                  55                  60

Asp Pro Tyr Cys Gln Ala Lys Tyr Thr Phe Cys Pro Thr Gly Ser Pro
65                  70                  75                  80

Ile Pro Val Met Lys Asp Asp Val Ile Glu Val Phe Arg Leu Gln
                85                  90                  95

Ala Pro Val Trp Glu Phe Lys Tyr Gly Asp Leu Leu Gly His Leu Lys
                100                 105                 110

Ile Met His Asp Ala Ile Gly Phe Arg Ser Thr Leu Thr Asp Lys Asn
            115                 120                 125

Tyr Thr Met Glu Trp Tyr Glu Leu Phe Gln Leu Gly Asn Cys Thr Phe
    130                 135                 140

Pro His Leu Arg Pro Glu Met Asn Ala Pro Phe Trp Cys Asn Gln Gly
145                 150                 155                 160
```

```
Ala Ala Cys Phe Phe Glu Gly Ile Asp Asp Asn His Trp Lys Glu Asn
            165                 170                 175

Gly Thr Leu Val Leu Val Ala Thr Ile Ser Gly Asn Met Phe Asn Lys
        180                 185                 190

Met Ala Gln Trp Val Lys Gln Asp Asn Glu Thr Gly Ile Tyr Tyr Glu
        195                 200                 205

Thr Trp Thr Val Gln Ala Ser Pro Glu Lys Gly Ala Glu Thr Trp Phe
    210                 215                 220

Glu Ser Tyr Asp Cys Ser Lys Phe Val Leu Arg Thr Tyr Glu Lys Leu
225                 230                 235                 240

Ala Glu Leu Gly Ala Glu Phe Lys Lys Thr Glu Thr Asn Tyr Thr Arg
                245                 250                 255

Ile Phe Leu Tyr Ser Gly Glu Pro Thr Tyr Leu Gly Asn Glu Thr Ser
            260                 265                 270

Ile Phe Gly Pro Thr Gly Asn Lys Thr Leu Ala Leu Ala Ile Lys Arg
        275                 280                 285

Phe Tyr Tyr Pro Phe Lys Pro His Leu Ser Thr Lys Glu Phe Leu Leu
    290                 295                 300

Ser Leu Leu Gln Ile Phe Asp Ala Val Ile Ile His Arg Gln Phe Tyr
305                 310                 315                 320

Leu Phe Tyr Asn Phe Glu Tyr Trp Phe Leu Pro Met Lys Phe Pro Phe
                325                 330                 335

Ile Lys Ile Thr Tyr Glu Glu Ile Pro Leu Pro Gln Arg Asn Lys Thr
            340                 345                 350

Tyr Phe Gly Leu
            355

<210> SEQ ID NO 8
<211> LENGTH: 350
<212> TYPE: PRT
<213> ORGANISM: Canis familiaris

<400> SEQUENCE: 8

Met Ala Gln Ala Gly Ser Ala Asp Pro Gly Val Gly Gly His Trp Ala
1               5                   10                  15

Ala Gly Pro Arg Cys Ala Pro Trp Arg Trp Ala Leu Ala Leu Leu Trp
            20                  25                  30

Leu Ala Thr Ala Ala Gly Gly Pro Ser Arg Arg Gln Trp Pro Val Pro
        35                  40                  45

Tyr Lys Arg Phe Ser Phe Arg Pro Glu Pro Asp Pro Tyr Cys Gln Ala
    50                  55                  60

Lys Tyr Thr Phe Cys Pro Thr Gly Ser Pro Ile Pro Val Met Lys Gly
65                  70                  75                  80

Asp Asp Val Ile Glu Val Phe Arg Leu Gln Thr Pro Val Trp Glu Phe
                85                  90                  95

Lys Tyr Gly Asn Leu Leu Gly His Leu Lys Ile Met His Asp Ala Ile
            100                 105                 110

Gly Phe Lys Ser Thr Leu Thr Gly Lys Asn Tyr Thr Met Glu Trp Tyr
        115                 120                 125

Glu Leu Phe Gln Leu Gly Asn Cys Thr Phe Pro His Leu Arg Pro Glu
    130                 135                 140

Met Asn Ala Pro Phe Trp Cys Asn Gln Gly Ala Ala Cys Phe Phe Glu
145                 150                 155                 160

Gly Ile Asp Asp Ile His Trp Lys Glu Asn Gly Thr Leu Val Leu Val
                165                 170                 175
```

-continued

```
Ala Thr Ile Ser Gly Asn Thr Phe Asn Gln Met Ala Lys Trp Val Lys
            180                 185                 190

Arg Asp Asn Glu Thr Gly Ile Tyr Tyr Glu Thr Trp Thr Val Gln Ala
        195                 200                 205

Ser Pro Thr Lys Gly Ala Glu Thr Trp Phe Gly Ser Tyr Asp Cys Ser
    210                 215                 220

Lys Phe Val Leu Arg Thr Tyr Lys Lys Leu Ala Glu Leu Gly Ala Glu
225                 230                 235                 240

Phe Lys Lys Ile Glu Thr Asn Tyr Thr Arg Ile Phe Leu Tyr Ser Gly
                245                 250                 255

Glu Pro Thr Tyr Leu Gly Asn Glu Thr Ser Ile Phe Gly Pro Thr Gly
            260                 265                 270

Asn Lys Thr Leu Ala Leu Ala Ile Lys Arg Phe Tyr Tyr Pro Phe Lys
        275                 280                 285

Pro His Leu Ser Thr Lys Glu Phe Leu Leu Ser Ile Leu Gln Ile Phe
    290                 295                 300

Asp Ala Val Ile Ile His Arg Glu Phe Tyr Leu Phe Tyr Asn Phe Glu
305                 310                 315                 320

Tyr Trp Phe Leu Pro Met Lys Phe Pro Phe Ile Lys Ile Thr Tyr Glu
                325                 330                 335

Glu Ile Pro Leu Pro Lys Arg Asn Glu Thr Leu Ser Gly Leu
            340                 345                 350

<210> SEQ ID NO 9
<211> LENGTH: 22
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 9
tgatgacagg ctggatctca cg                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 10
acaggtgaca cttggcatga gc                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 11
tttgctttgg tgttcacata gg                                              22

<210> SEQ ID NO 12
<211> LENGTH: 22
<212> TYPE: DNA
<213> ORGANISM: Artificial Sequence
```

```
<220> FEATURE:
<223> OTHER INFORMATION: Synthetically prepared oligonucleotide primer
      sequence

<400> SEQUENCE: 12
tttgctttgg tgttcacata gg                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 13
tgtgcaagaa gaaccaaact cc                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 14
tctgagataa gcagcaatgg tc                                              22

<210> SEQ ID NO 15
<211> LENGTH: 20
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 15
ttctgctcca aggcagaaag                                                 20

<210> SEQ ID NO 16
<211> LENGTH: 21
<212> TYPE: DNA
<213> ORGANISM: Artificial Sequence
<220> FEATURE:
<223> OTHER INFORMATION: Synthetically prepared oligonucleotide primer
      sequence

<400> SEQUENCE: 16
cccaagtagg taggttctcc a                                               21

<210> SEQ ID NO 17
<211> LENGTH: 1053
<212> TYPE: DNA
<213> ORGANISM: Canis familiaris
<220> FEATURE:
<221> NAME/KEY: CDS
<222> LOCATION: (1)...(621)

<400> SEQUENCE: 17 atg gcg cag gcg ggg agc gcc gac ccc ggg gtc ggg ggc cat tgg gcc       48
Met Ala Gln Ala Gly Ser Ala Asp Pro Gly Val Gly Gly His Trp Ala
 1               5                  10                  15 gcg ggg cct cgg tgc gcg cct tgg cgc tgg gcc ctg gcg ctg ctg tgg       96
Ala Gly Pro Arg Cys Ala Pro Trp Arg Trp Ala Leu Ala Leu Leu Trp
             20                  25                  30
```

```
ctg gcg acg gcc gcg ggc ggc ccc tcc cgg cgc cag tgg ccc gtg ccc      144
Leu Ala Thr Ala Ala Gly Gly Pro Ser Arg Arg Gln Trp Pro Val Pro
        35                  40                  45 tac aag cgc ttt tcc ttc cgt cca gaa cca gat cct tat tgt caa gct      192
Tyr Lys Arg Phe Ser Phe Arg Pro Glu Pro Asp Pro Tyr Cys Gln Ala
50                  55                  60 aaa tac aca ttc tgt cca act ggc tca cct atc cca gtt atg aaa ggt      240
Lys Tyr Thr Phe Cys Pro Thr Gly Ser Pro Ile Pro Val Met Lys Gly
 65                  70                  75                  80 gat gat gtc att gaa gtc ttc cgg tta caa acc cca gta tgg gaa ttt      288
Asp Asp Val Ile Glu Val Phe Arg Leu Gln Thr Pro Val Trp Glu Phe
                85                  90                  95 aaa tat ggg aac ctc ctg gga cac ttg aaa att atg cat gat gcc att      336
Lys Tyr Gly Asn Leu Leu Gly His Leu Lys Ile Met His Asp Ala Ile
            100                 105                 110 gga ttc aag agt act tta act ggc aag aac tac aca atg gaa tgg tat      384
Gly Phe Lys Ser Thr Leu Thr Gly Lys Asn Tyr Thr Met Glu Trp Tyr
        115                 120                 125 gaa ctt ttc caa ctt gga aac tgt aca ttt ccc cat ctc cga cct gaa      432
Glu Leu Phe Gln Leu Gly Asn Cys Thr Phe Pro His Leu Arg Pro Glu
    130                 135                 140 atg aat gcc cct ttc tgg tgc aat caa ggc gct gcc tgt ttt ttt gaa      480
Met Asn Ala Pro Phe Trp Cys Asn Gln Gly Ala Ala Cys Phe Phe Glu
145                 150                 155                 160 ggg att gat gat atc cac tgg aag gaa aat ggg acg tta gta ctg gta      528
Gly Ile Asp Asp Ile His Trp Lys Glu Asn Gly Thr Leu Val Leu Val
                165                 170                 175 gca acc ata tca gga aac aca ttt aac caa atg gca aag tgg gta aag      576
Ala Thr Ile Ser Gly Asn Thr Phe Asn Gln Met Ala Lys Trp Val Lys
            180                 185                 190 cgg gac aat gaa aca gga att tat tac gag acg tgg act gtt taa          621
Arg Asp Asn Glu Thr Gly Ile Tyr Tyr Glu Thr Trp Thr Val   *
        195                 200                 205 gccagcccaa caaggggggc tgagacatgg tttgaatcct atgattgttc taaattcgtg     681
ttaaggacat acaagaagtt ggctgaactt ggagcagagt tcaagaagat agaaaccaac     741
tatacaagaa tatttcttta cagtggagaa cctacctact tgggaaatga aacctctatt     801
tttgggccga caggaaataa gactcttgct tagccataaa aagattttta ttacccttc      861 aaaccacatt tatcaactaa agaatttctg ctcagtatct tgcaaatttt tgatgcagtg     921
attatacaca gagagtttta tttgttttat aattttgaat attggttttt acctatgaaa     981
tttcctttta ttaaaataac atatgaagaa atcccttac ctaaaagaaa tgaaacactt     1041
tctggtctat aa                                                       1053
```

<210> SEQ ID NO 18
<211> LENGTH: 206
<212> TYPE: PRT
<213> ORGANISM: Canis familiaris

<400> SEQUENCE: 18

```
Met Ala Gln Ala Gly Ser Ala Asp Pro Gly Val Gly Gly His Trp Ala
 1               5                  10                  15

Ala Gly Pro Arg Cys Ala Pro Trp Arg Trp Ala Leu Ala Leu Leu Trp
            20                  25                  30

Leu Ala Thr Ala Ala Gly Gly Pro Ser Arg Arg Gln Trp Pro Val Pro
        35                  40                  45

Tyr Lys Arg Phe Ser Phe Arg Pro Glu Pro Asp Pro Tyr Cys Gln Ala
    50                  55                  60
```

-continued

```
Lys Tyr Thr Phe Cys Pro Thr Gly Ser Pro Ile Pro Val Met Lys Gly
 65                  70                  75                  80

Asp Asp Val Ile Glu Val Phe Arg Leu Gln Thr Pro Val Trp Glu Phe
                 85                  90                  95

Lys Tyr Gly Asn Leu Leu Gly His Leu Lys Ile Met His Asp Ala Ile
            100                 105                 110

Gly Phe Lys Ser Thr Leu Thr Gly Lys Asn Tyr Thr Met Glu Trp Tyr
        115                 120                 125

Glu Leu Phe Gln Leu Gly Asn Cys Thr Phe Pro His Leu Arg Pro Glu
    130                 135                 140

Met Asn Ala Pro Phe Trp Cys Asn Gln Gly Ala Ala Cys Phe Phe Glu
145                 150                 155                 160

Gly Ile Asp Asp Ile His Trp Lys Glu Asn Gly Thr Leu Val Leu Val
                165                 170                 175

Ala Thr Ile Ser Gly Asn Thr Phe Asn Gln Met Ala Lys Trp Val Lys
            180                 185                 190

Arg Asp Asn Glu Thr Gly Ile Tyr Tyr Glu Thr Trp Thr Val
        195                 200                 205

<210> SEQ ID NO 19
<211> LENGTH: 8
<212> TYPE: DNA
<213> ORGANISM: Canis familiares

<400> SEQUENCE: 19 tgttcaag                                                              8

<210> SEQ ID NO 20
<211> LENGTH: 7
<212> TYPE: PRT
<213> ORGANISM: Canis familiares

<400> SEQUENCE: 20

Thr Thr Thr Val Gln Ala Ser
 1               5
```